US006482608B1

(12) United States Patent
Perrin et al.

(10) Patent No.: US 6,482,608 B1
(45) Date of Patent: *Nov. 19, 2002

(54) CLONING AND RECOMBINANT PRODUCTION OF CRF RECEPTOR(S)

(75) Inventors: Marilyn H. Perrin, La Jolla; Ruoping Chen, San Diego; Kathy A. Lewis, San Diego; Wylie W. Vale, Jr., La Jolla; Cynthia J. Donaldson, San Diego; Paul Sawchenko, Encinitas, all of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,734

(22) Filed: May 26, 2000

Related U.S. Application Data

(60) Division of application No. 09/191,724, filed on Nov. 12, 1998, which is a continuation-in-part of application No. 08/483,139, filed on Jun. 7, 1995, now abandoned, which is a division of application No. 08/374,009, filed on Jan. 17, 1995, which is a continuation-in-part of application No. 08/353,537, filed on Dec. 9, 1994, now abandoned, which is a continuation-in-part of application No. PCT/US94/05908, filed on May 25, 1994, which is a continuation-in-part of application No. 08/110,286, filed on Aug. 23, 1993, now Pat. No. 5,728,545, which is a continuation-in-part of application No. 08/079,320, filed on Jun. 18, 1993, now abandoned.

(51) Int. Cl.[7] .............................. C12N 5/10; C12P 21/02

(52) U.S. Cl. ...................... 435/69.1; 435/325; 530/350; 536/23.5

(58) Field of Search ................................ 435/69.1, 325; 530/350; 536/23.5

(56) References Cited

U.S. PATENT DOCUMENTS

| | | | |
|---|---|---|---|
| 3,654,090 A | * | 4/1972 | Wilhelmus et al. |
| 3,773,919 A | * | 11/1973 | Boswell et al. |
| 3,850,752 A | * | 11/1974 | Schuurs et al. |
| 4,016,043 A | * | 4/1977 | Schuurs et al. |
| 4,415,558 A | * | 11/1983 | Vale, Jr. et al. |
| 4,489,163 A | * | 12/1984 | Rivier et al. |
| 4,493,795 A | * | 1/1985 | Nestor, Jr. et al. |
| 4,525,189 A | * | 6/1985 | Ohmi et al. |
| 4,533,654 A | * | 8/1985 | Lederis et al. |
| 4,594,329 A | * | 6/1986 | Vale, Jr. et al. |
| 4,605,642 A | * | 8/1986 | Rivier et al. |
| 4,837,148 A | * | 6/1989 | Cregg |
| 4,855,231 A | * | 8/1989 | Stoman et al. |
| 4,882,279 A | * | 11/1989 | Cregg |
| 4,908,352 A | * | 3/1990 | Lederis et al. |
| 4,929,555 A | * | 5/1990 | Cregg et al. |
| 4,952,496 A | * | 8/1990 | Studier et al. |
| 5,055,396 A | * | 10/1991 | Curtiss et al. |
| 5,109,111 A | * | 4/1992 | Rivier et al. |

OTHER PUBLICATIONS

Berridge and Dunn, "CRF and Restraint–Stress Decrease Exploratory Behavior in Hypophysectomized Mice," *Pharmacology Biochemistry & Behavior*, 34:517–519 (1989).

Britton et al., "Activating and 'Anxiogenic' Effects of Corticotropin Releasing Factor Are Not Inhibited by Blockade of the Pituitary–Adrenal System with Dexamethasone," *Life Sciences*, 39:1281–1286 (1986).

Britton et al., "Dexamethasone Suppresses Pituitary–Adrenal But Not Behavioral Effects of Centrally Administered CRF," *Life Sciences*, 38:211–216 (1986).

Brown and Fisher, "Central Nervous System Effects of Corticotropin Releasing Factor in the Dog," *Brain Research*, 280:75–79 (1983).

Butler et al., "Corticotropin–Releasing Factor Produces Fear–Enhancing and Behavioral Activating Effects Following Infusion into the Locus Coeruleus," *The Journal of Neuroscience*, 10(1):176–183 (1990).

Duffaud et al., "Expression and Secretion of Foreign Proteins in *Escherichia coli*," *Method in Enzymology*, 153:492–507 (1987).

Fabbri et al., "Corticotropin–Releasing Factor is Produced by Rat Leydig Cells and has a Major Local Antireproductive Role in the Testis," *Endocrinology*, 127(3):1541–1543 (1990).

Galfre and Milstein, "Preparation of Monoclonal Antibodies Strategies and Procedures," *Methods in Enzymology*, 73:3–46 (1981).

Gearing et al., "Expression cloning of a receptor for human granulocyte–macrophage colony–stimulating factor," *The EMBO Journal*, 8(12):3667–3676 (1989).

Grunt et al., "Dilatory and Inotropic Effects of Corticotropin–Releasing Factor (CRF) on the Isolated Heart," *Horm. Metab. Res.*, 24:56–59 (1990).

Hanani and Wood, "Corticotropin–releasing hormone excites myenteric neurons in the guinea–pig small intestine," *European Journal of Pharmacology*, 211:23–27 (1992).

(List continued on next page.)

*Primary Examiner*—Gary L. Kunz
*Assistant Examiner*—Stephen Gucker
(74) *Attorney, Agent, or Firm*—Foley & Lardner; Stephen E. Reiter

(57) ABSTRACT

In accordance with the present invention, there are provided novel G-protein-coupled receptor proteins (CRF-R) characterized by having sufficient binding affinity for corticotropin releasing factor (CRF) such that concentrations of 10 nM of CRF occupy 50% of the binding sites of said receptor protein. Nucleic acid sequences encoding such receptors, assays employing same, as well as antibodies derived therefrom, are also disclosed. Invention CRF-Rs can be employed in a variety of ways, such as, for example, in bioassays, for production of antibodies thereto, in therapeutic compositions containing such proteins and/or antibodies.

3 Claims, 8 Drawing Sheets

OTHER PUBLICATIONS

Imaki et al., "Widespread expression of corticotropin–releasing factor messenger RNA and immunoreactivity in the rat olfactory bulb," *Brain Research*, 496:35–44 (1989).

Kawahito et al., Local Secretion of Corticotropin–Releasing Hormone by Enterochromaffin Cells in Human Colon, *Gastroenterology*, 106:859–865 (1994).

Kozak, M., "Structural Features in Eukaryotic mRNAs That Modulate the Initiation of Translation," *The Journal of Biological Chemistry*, 266(30):19867–19870 (1991).

Linder and Gilman, "G Proteins, Tucked into the internal surface of the cell's outer membrane, these versatile molecules coordinate cellular responses to a multitude of signals that impinge from without," *Scientific American*, 56–65 (1992).

Mamula and Goldfine, "Cloning and Characterization of the Human Insulin–Like Growth Factor–I Receptor Gene 5'–Flanking Region," *DNA and Cell Biology*, 11(1):43–50 (1992).

Munson and Rodbard, "Ligand: A Versatile Computerized Approach for Characterization of Ligand–Binding Systems," *Analytical Biochemistry*, 107:220–239 (1980).

Nieuwenhuijzen Kruseman et al., "Corticotropin–Releasing Factor Immunoreactivity in Human Gastrointestinal Tract," *The Lancet*, 2:1245–1246 (1982).

Pearson and Lipman, "Improved tools for biological sequence comparison," *Proc. Nat. Acad. Sci.*, 85:2444–2448 (1988).

Perrin et al., "Corticotropin–Releasing Factor Binding to the Anterior Pituitary Receptor Is Modulated by Divalent Cations and Guanyl Nucleotides," *Endocrinology*, 118(3):1171–1179 (1986).

Petrusz et al., "Central and peripheral distribution of corticotropin–releasing factor," *Federation Proc.*, 44:229–235 (1985).

Potter et al., "The central distribution of a corticotropin–releasing factor (CRF)–binding protein predicts multiple sites and modes on interaction with CRF," *Proc. Natl. Acad. Sci. USA*, 89:4192–4196 (1992).

Rodwell and McKearn, "Linker Technology: Antibody–Mediated Delivery Systems," *Bio/Technology*, 3:889–894 (1985).

Saitoh et al., "Effect of Corticotropin–Releasing Factor on the Electrical and Mechanical Activities of the Guinea–Pig Ventricular Myocardium," *Gen. Pharmac.*, 21(3):337–342 (1990).

Sheldon et al., "Gastrointestinal motor effects of corticotropin–releasing factor in mice," *Regulatory Peptides*, 28:137–151 (1990).

Simon et al., "Diversity of G Proteins in Signal Transduction," *Science*, 252:802–808 (1991).

Stephens et al., "Interacisternal Injection of CRF Antagonist Blocks Surgical Stress–Induced Inhibition of Gastric Secretion in the Rat," *Peptides, vol. 9*, 1067–1070 (1988).

Suda et al., "Immunoreactive Corticotropin and Corticotropin–Releasing Factor in Human Hypothalamus, Adrenal, Lung Cancer, and Pheochromocytoma," *Journal of Clinical Endocrinology and Metabolism*, 58(5):919–924 (1984).

Sutton et al., "Corticotropin releasing factor produces behavioural activation in rats," *Nature*, 297:331–333 (1982).

Swanson et al., "Organization of Ovine Corticotropin–Releasing Factor Immunoreactive Cells and Fibers in the Rat Brain: An Immunohistochemical Study," *Neuroendocrinology*, 36:165–186 (1983).

Vale et al., "Characterization of a 41–Residue Ovine Hypothalamic Peptide That Stimulates Secretion of Corticotropin and β–Endorphin," *Science*, 213:1394–1397 (1981).

Vaughn et al., "Detection and Purification of Inhibin Using Antisera Generated against Synthetic Peptide Fragments," *Methods in Enzymology*, 168:588–617 (1989).

William et al., "Corticotropin–releasing factor directly mediates colonic responses to stress," *Am. J. Physiol.*, 253:G582–G586 (1987).

Yoon et al., "Presence of Immunoreactive Corticotropin–Releasing Factor in Rat Testis," *Endocrinology*, 122(3):759–761 (1988).

* cited by examiner

SEQUENCE LISTING

<160> NUMBER OF SEQ ID NOS: 15

<210> SEQ ID NO 1
<211> LENGTH: 1495
<212> TYPE: DNA
<213> ORGANISM: Homo sapiens
<220> FEATURE:
<221> NAME/KEY: CDS
<222> LOCATION: (82)...(1326)
<223> OTHER INFORMATION: /product = "Human pituitary CRF-receptor"
     /note= "This sequence is encoded by clone
     "CRF-R1"."

<400> SEQUENCE: 1

```
cgagcccgca gccgcccgcc ggttcctctg ggatgtccgt aggacccggg cattcaggac        60
ggtagccgag cgagcccgag g atg gga ggg cac ccg cag ctc cgt ctc gtc       111
                        Met Gly Gly His Pro Gln Leu Arg Leu Val
                         1               5                  10 aag gcc ctt ctc ctt ctg ggg ctg aac ccc gtc tct gcc tcc ctc cag       159
Lys Ala Leu Leu Leu Leu Gly Leu Asn Pro Val Ser Ala Ser Leu Gln
             15                  20                  25 gac cag cac tgc gag agc ctg tcc ctg gcc agc aac atc tca gga ctg       207
Asp Gln His Cys Glu Ser Leu Ser Leu Ala Ser Asn Ile Ser Gly Leu
         30                  35                  40 cag tgc aac gca tcc gtg gac ctc att ggc acc tgc tgg ccc cgc agc       255
Gln Cys Asn Ala Ser Val Asp Leu Ile Gly Thr Cys Trp Pro Arg Ser
     45                  50                  55 cct gcg ggg cag cta gtg gtt cgg ccc tgc cct gcc ttt ttc tat ggt       303
Pro Ala Gly Gln Leu Val Val Arg Pro Cys Pro Ala Phe Phe Tyr Gly
 60                  65                  70 gtc cgc tac aat acc aca aac aat ggc tac cgg gag tgc ctg gcc aat       351
Val Arg Tyr Asn Thr Thr Asn Asn Gly Tyr Arg Glu Cys Leu Ala Asn
 75                  80                  85                  90 ggc agc tgg gcc gcc cgc gtg aat tac tcc gag tgc cag gag atc ctc       399
Gly Ser Trp Ala Ala Arg Val Asn Tyr Ser Glu Cys Gln Glu Ile Leu
             95                 100                 105 aat gag gag aaa aaa agc aag gtg cac tac cat gtc gca gtc atc atc       447
Asn Glu Glu Lys Lys Ser Lys Val His Tyr His Val Ala Val Ile Ile
         110                 115                 120 aac tac ctg ggc cac tgt atc tcc ctg gtg gcc ctc ctg gtg gcc ttt       495
Asn Tyr Leu Gly His Cys Ile Ser Leu Val Ala Leu Leu Val Ala Phe
     125                 130                 135 gtc ctc ttt ctg cgg ctc agg agc atc cgg tgc ctg cga aac atc atc       543
Val Leu Phe Leu Arg Leu Arg Ser Ile Arg Cys Leu Arg Asn Ile Ile
 140                 145                 150 cac tgg aac ctc atc tcc gcc ttc atc ctg cgc aac gcc acc tgg ttc       591
His Trp Asn Leu Ile Ser Ala Phe Ile Leu Arg Asn Ala Thr Trp Phe
155                 160                 165                 170 gtg gtc cag cta acc atg agc ccc gag gtc cac cag agc aac gtg ggc       639
Val Val Gln Leu Thr Met Ser Pro Glu Val His Gln Ser Asn Val Gly
             175                 180                 185 tgg tgc agg ttg gtg aca gcc gcc tac aac tac ttc cat gtg acc aac       687
Trp Cys Arg Leu Val Thr Ala Ala Tyr Asn Tyr Phe His Val Thr Asn
         190                 195                 200 ttc ttc tgg atg ttc ggc gag ggc tgc tac ctg cac aca gcc atc gtg       735
Phe Phe Trp Met Phe Gly Glu Gly Cys Tyr Leu His Thr Ala Ile Val
     205                 210                 215 ctc acc tac tcc act gac cgg ctg cgc aaa tgg atg ttc atc tgc att       783
Leu Thr Tyr Ser Thr Asp Arg Leu Arg Lys Trp Met Phe Ile Cys Ile
 220                 225                 230
```

-continued

```
ggc tgg ggt gtg ccc ttc ccc atc att gtg gcc tgg gcc att ggg aag      831
Gly Trp Gly Val Pro Phe Pro Ile Ile Val Ala Trp Ala Ile Gly Lys
235                 240                 245                 250 ctg tac tac gac aat gag aag tgc tgg ttt ggc aaa agg cct ggg gtg      879
Leu Tyr Tyr Asp Asn Glu Lys Cys Trp Phe Gly Lys Arg Pro Gly Val
                255                 260                 265 tac acc gac tac atc tac cag ggc ccc atg atc ctg gtc ctg ctg atc      927
Tyr Thr Asp Tyr Ile Tyr Gln Gly Pro Met Ile Leu Val Leu Leu Ile
            270                 275                 280 aat ttc atc ttc ctt ttc aac atc gtc cgc atc ctc atg acc aag ctc      975
Asn Phe Ile Phe Leu Phe Asn Ile Val Arg Ile Leu Met Thr Lys Leu
        285                 290                 295 cgg gca tcc acc acg tct gag acc att cag tac agg aag gct gtg aaa     1023
Arg Ala Ser Thr Thr Ser Glu Thr Ile Gln Tyr Arg Lys Ala Val Lys
    300                 305                 310 gcc act ctg gtg ctg ctg ccc ctc ctg ggc atc acc tac atg ctg ttc     1071
Ala Thr Leu Val Leu Leu Pro Leu Leu Gly Ile Thr Tyr Met Leu Phe
315                 320                 325                 330 ttc gtc aat ccc ggg gag gat gag gtc tcc cgg gtc gtc ttc atc tac     1119
Phe Val Asn Pro Gly Glu Asp Glu Val Ser Arg Val Val Phe Ile Tyr
                335                 340                 345 ttc aac tcc ttc ctg gaa tcc ttc cag ggc ttc ttt gtg tct gtg ttc     1167
Phe Asn Ser Phe Leu Glu Ser Phe Gln Gly Phe Phe Val Ser Val Phe
            350                 355                 360 tac tgt ttc ctc aat agt gag gtc cgt tct gcc atc cgg aag agg tgg     1215
Tyr Cys Phe Leu Asn Ser Glu Val Arg Ser Ala Ile Arg Lys Arg Trp
        365                 370                 375 cac cgg tgg cag gac aag cac tcg atc cgt gcc cga gtg gcc cgt gcc     1263
His Arg Trp Gln Asp Lys His Ser Ile Arg Ala Arg Val Ala Arg Ala
    380                 385                 390 atg tcc atc ccc acc tcc cca acc cgt gtc agc ttt cac agc atc aag     1311
Met Ser Ile Pro Thr Ser Pro Thr Arg Val Ser Phe His Ser Ile Lys
395                 400                 405                 410 cag tcc aca gca gtc tgagctggca ggtcatggag cagcccccaa agagctgtgg     1366
Gln Ser Thr Ala Val
                415 ctgggggggat gacggccagg ctccctgacc accctgcctg tggaggtgac ctgttaggtc   1426
tcatgcccac tccccagga gcagctggca ctgacagcct ggggggggccg ctctcccct    1486 gcagccgtg                                                           1495
```

<210> SEQ ID NO 2
<211> LENGTH: 415
<212> TYPE: PRT
<213> ORGANISM: Homo sapiens

<400> SEQUENCE: 2

Met Gly Gly His Pro Gln Leu Arg Leu Val Lys Ala Leu Leu Leu Leu
 1               5                  10                  15

Gly Leu Asn Pro Val Ser Ala Ser Leu Gln Asp Gln His Cys Glu Ser
                20                  25                  30

Leu Ser Leu Ala Ser Asn Ile Ser Gly Leu Gln Cys Asn Ala Ser Val
            35                  40                  45

Asp Leu Ile Gly Thr Cys Trp Pro Arg Ser Pro Ala Gly Gln Leu Val
        50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg

|  |  |  |  |  | 85 |  |  |  |  | 90 |  |  |  |  | 95 |  |
|---|---|---|---|---|---|---|---|---|---|---|---|---|---|---|---|---|

Val Asn Tyr Ser Glu Cys Gln Glu Ile Leu Asn Glu Lys Lys Ser
                100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
                180                 185                 190

Ala Ala Tyr Asn Tyr Phe His Val Thr Asn Phe Phe Trp Met Phe Gly
                195                 200                 205

Glu Gly Cys Tyr Leu His Thr Ala Ile Val Leu Thr Tyr Ser Thr Asp
    210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
                260                 265                 270

Gln Gly Pro Met Ile Leu Val Leu Leu Ile Asn Phe Ile Phe Leu Phe
            275                 280                 285

Asn Ile Val Arg Ile Leu Met Thr Lys Leu Arg Ala Ser Thr Thr Ser
290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
                340                 345                 350

Ser Phe Gln Gly Phe Phe Val Ser Val Phe Tyr Cys Phe Leu Asn Ser
            355                 360                 365

Glu Val Arg Ser Ala Ile Arg Lys Arg Trp His Arg Trp Gln Asp Lys
370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415

<210> SEQ ID NO 3
<211> LENGTH: 87
<212> TYPE: DNA
<213> ORGANISM: Homo sapiens
<220> FEATURE:
<221> NAME/KEY: CDS
<222> LOCATION: (1)...(87)
<223> OTHER INFORMATION: CRF-R splice variant insert fragment

<400> SEQUENCE: 3 cca ggc tgc acc cat tgg ggt gac cag gca gat gga gcc ctg gag gtg    48
Pro Gly Cys Thr His Trp Gly Asp Gln Ala Asp Gly Ala Leu Glu Val
 1               5                  10                  15 ggg gct cca tgg agt ggt gcc cca ttt cag gtt cga agg                87

```
Gly Ala Pro Trp Ser Gly Ala Pro Phe Gln Val Arg Arg
            20                  25

<210> SEQ ID NO 4
<211> LENGTH: 29
<212> TYPE: PRT
<213> ORGANISM: Homo sapiens

<400> SEQUENCE: 4

Pro Gly Cys Thr His Trp Gly Asp Gln Ala Asp Gly Ala Leu Glu Val
  1               5                  10                  15

Gly Ala Pro Trp Ser Gly Ala Pro Phe Gln Val Arg Arg
            20                  25

<210> SEQ ID NO 5
<211> LENGTH: 1411
<212> TYPE: DNA
<213> ORGANISM: Rattus
<220> FEATURE:
<221> NAME/KEY: CDS
<222> LOCATION: (80)...(1324)

<400> SEQUENCE: 5
agaccgcagc cgcccgccct ccgctctggg atgtcggagc gatccaggca tccaggacgc      60
tgacggagcg agcccgagg atg gga cgg cgc ccg cag ctc cgg ctc gtg aag     112
              Met Gly Arg Arg Pro Gln Leu Arg Leu Val Lys
                1               5                  10 gcc ctt ctc ctt ctg ggg ctg aac cct gtg tcc acc tcc ctt cag gat     160
Ala Leu Leu Leu Leu Gly Leu Asn Pro Val Ser Thr Ser Leu Gln Asp
            15                  20                  25 cag cgc tgt gag aac ctg tcc ctg acc agc aat gtt tct ggc ctg cag     208
Gln Arg Cys Glu Asn Leu Ser Leu Thr Ser Asn Val Ser Gly Leu Gln
         30                  35                  40 tgc aat gca tcc gtg gac ctc att ggc acc tgc tgg ccc cgg agc cct     256
Cys Asn Ala Ser Val Asp Leu Ile Gly Thr Cys Trp Pro Arg Ser Pro
     45                  50                  55 gcg ggc cag ttg gtg gtc cga ccc tgc cct gcc ttt ttc tac ggt gtc     304
Ala Gly Gln Leu Val Val Arg Pro Cys Pro Ala Phe Phe Tyr Gly Val
 60                  65                  70                  75 cgc tac aac acg aca aac aat ggc tac cgg gag tgc ctg gcc aac ggc     352
Arg Tyr Asn Thr Thr Asn Asn Gly Tyr Arg Glu Cys Leu Ala Asn Gly
                 80                  85                  90 agc tgg gca gcc cgt gtg aat tat tct gag tgc cag gag att ctc aac     400
Ser Trp Ala Ala Arg Val Asn Tyr Ser Glu Cys Gln Glu Ile Leu Asn
             95                 100                 105 gaa gag aag aag agc aaa gta cac tac cat gtt gca gtc atc atc aac     448
Glu Glu Lys Lys Ser Lys Val His Tyr His Val Ala Val Ile Ile Asn
         110                 115                 120 tac ctg ggt cac tgc atc tcc ctg gta gcc ctc ctg gtg gcc ttt gtc     496
Tyr Leu Gly His Cys Ile Ser Leu Val Ala Leu Leu Val Ala Phe Val
     125                 130                 135 ctc ttc ttg cgg ctc agg agc atc cgg tgc ctg aga aac atc atc cac     544
Leu Phe Leu Arg Leu Arg Ser Ile Arg Cys Leu Arg Asn Ile Ile His
140                 145                 150                 155 tgg aac ctc atc tcg gct ttc atc cta cgc aac gcc acg tgg ttt gtg     592
Trp Asn Leu Ile Ser Ala Phe Ile Leu Arg Asn Ala Thr Trp Phe Val
                160                 165                 170 gtc cag ctc acc gtg agc ccc gag gtg cac cag agc aat gtg gcc tgg     640
Val Gln Leu Thr Val Ser Pro Glu Val His Gln Ser Asn Val Ala Trp
            175                 180                 185 tgt agg ttg gtg aca gcc gcc tac aat tac ttc cat gta acc aac ttc     688
```

-continued

```
                    Cys Arg Leu Val Thr Ala Ala Tyr Asn Tyr Phe His Val Thr Asn Phe
                                    190                 195                 200 ttc tgg atg ttc ggt gag ggc tgc tac ctg cac aca gcc att gtg ctc        736
Phe Trp Met Phe Gly Glu Gly Cys Tyr Leu His Thr Ala Ile Val Leu
        205                 210                 215 acg tac tcc acc gac cgt ctg cgc aag tgg atg ttc gtc tgc att ggc        784
Thr Tyr Ser Thr Asp Arg Leu Arg Lys Trp Met Phe Val Cys Ile Gly
220                 225                 230                 235 tgg ggt gta cct ttc ccc atc att gtg gct tgg gcc att ggg aag ctg        832
Trp Gly Val Pro Phe Pro Ile Ile Val Ala Trp Ala Ile Gly Lys Leu
                240                 245                 250 cac tac gac aat gaa aag tgc tgg ttt ggc aaa cgt cct ggg gta tac        880
His Tyr Asp Asn Glu Lys Cys Trp Phe Gly Lys Arg Pro Gly Val Tyr
            255                 260                 265 act gac tac atc tac cag ggc ccc atg atc ctg gtc ctg ctg atc aac        928
Thr Asp Tyr Ile Tyr Gln Gly Pro Met Ile Leu Val Leu Leu Ile Asn
        270                 275                 280 ttt atc ttt ctc ttc aac att gtc cgc atc ctc atg acc aaa ctc cgg        976
Phe Ile Phe Leu Phe Asn Ile Val Arg Ile Leu Met Thr Lys Leu Arg
285                 290                 295 gca tcc act aca tct gag acc att cag tac agg aag gct gtg aag gcc       1024
Ala Ser Thr Thr Ser Glu Thr Ile Gln Tyr Arg Lys Ala Val Lys Ala
300                 305                 310                 315 act ctg gtg ctc ctg ccc ctt ctg ggc atc acc tac atg ttg ttc ttc       1072
Thr Leu Val Leu Leu Pro Leu Leu Gly Ile Thr Tyr Met Leu Phe Phe
                320                 325                 330 gtc aac cct gga gag gac gag gtc tcc agg gtc gtc ttc atc tac ttc       1120
Val Asn Pro Gly Glu Asp Glu Val Ser Arg Val Val Phe Ile Tyr Phe
            335                 340                 345 aac tct ttt ctg gag tcc ttt cag ggc ttc ttt gtg tct gtg ttc tac       1168
Asn Ser Phe Leu Glu Ser Phe Gln Gly Phe Phe Val Ser Val Phe Tyr
        350                 355                 360 tgt ttt ctg aac agt gag gtc cgc tcc gct atc cgg aag agg tgg cgt       1216
Cys Phe Leu Asn Ser Glu Val Arg Ser Ala Ile Arg Lys Arg Trp Arg
365                 370                 375 cgg tgg cag gac aag cac tcc atc aga gcc cga gtg gcc cga gct atg       1264
Arg Trp Gln Asp Lys His Ser Ile Arg Ala Arg Val Ala Arg Ala Met
380                 385                 390                 395 tcc atc ccc acc tcc ccg acc aga gtc agc ttt cac agc atc aag cag       1312
Ser Ile Pro Thr Ser Pro Thr Arg Val Ser Phe His Ser Ile Lys Gln
                400                 405                 410 tcc aca gca gtg tgagctccag gccacagagc agcccccaag acctgaggcc           1364
Ser Thr Ala Val
            415 ggggagatga tgcaagctca ctgacgagcc agtctgcaga cgcaagc                   1411
```

<210> SEQ ID NO 6
<211> LENGTH: 415
<212> TYPE: PRT
<213> ORGANISM: Rattus

<400> SEQUENCE: 6

```
Met Gly Arg Arg Pro Gln Leu Arg Leu Val Lys Ala Leu Leu Leu Leu
 1               5                  10                  15

Gly Leu Asn Pro Val Ser Thr Ser Leu Gln Asp Gln Arg Cys Glu Asn
                20                  25                  30

Leu Ser Leu Thr Ser Asn Val Ser Gly Leu Gln Cys Asn Ala Ser Val
            35                  40                  45

Asp Leu Ile Gly Thr Cys Trp Pro Arg Ser Pro Ala Gly Gln Leu Val
```

```
                50                  55                  60
Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Lys Lys Ser
                100                 105                 110

Lys Val His Tyr His Val Ala Val Ile Ile Asn Tyr Leu Gly His Cys
                115                 120                 125

Ile Ser Leu Val Ala Leu Leu Val Ala Phe Val Leu Phe Leu Arg Leu
            130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Val
                165                 170                 175

Ser Pro Glu Val His Gln Ser Asn Val Ala Trp Cys Arg Leu Val Thr
                180                 185                 190

Ala Ala Tyr Asn Tyr Phe His Val Thr Asn Phe Phe Trp Met Phe Gly
            195                 200                 205

Glu Gly Cys Tyr Leu His Thr Ala Ile Val Leu Thr Tyr Ser Thr Asp
210                 215                 220

Arg Leu Arg Lys Trp Met Phe Val Cys Ile Gly Trp Gly Val Pro Phe
225                 230                 235                 240

Pro Ile Ile Val Ala Trp Ala Ile Gly Lys Leu His Tyr Asp Asn Glu
                245                 250                 255

Lys Cys Trp Phe Gly Lys Arg Pro Gly Val Tyr Thr Asp Tyr Ile Tyr
                260                 265                 270

Gln Gly Pro Met Ile Leu Val Leu Leu Ile Asn Phe Ile Phe Leu Phe
            275                 280                 285

Asn Ile Val Arg Ile Leu Met Thr Lys Leu Arg Ala Ser Thr Thr Ser
290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
                340                 345                 350

Ser Phe Gln Gly Phe Phe Val Ser Val Phe Tyr Cys Phe Leu Asn Ser
            355                 360                 365

Glu Val Arg Ser Ala Ile Arg Lys Arg Trp Arg Trp Gln Asp Lys
                370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415

<210> SEQ ID NO 7
<211> LENGTH: 210
<212> TYPE: DNA
<213> ORGANISM: Mus musculus
<220> FEATURE:
<221> NAME/KEY: CDS
<222> LOCATION: (1)...(210)

<400> SEQUENCE: 7
```

```
tgg tgc cgc tgc atc acc acc atc ttc aac tat ttt gtg gtc acc aac      48
Trp Cys Arg Cys Ile Thr Thr Ile Phe Asn Tyr Phe Val Val Thr Asn
 1               5                  10                  15 ttc ttc tgg atg ttt gtg gag ggg tgc tac ctg cac acg gcc att gtc      96
Phe Phe Trp Met Phe Val Glu Gly Cys Tyr Leu His Thr Ala Ile Val
             20                  25                  30 atg acg tac tcc aca gag cac ctg cgc aag tgg ctt ttc ctc ttc att     144
Met Thr Tyr Ser Thr Glu His Leu Arg Lys Trp Leu Phe Leu Phe Ile
         35                  40                  45 gga tgg tgc att ccc tgc cct atc atc atc gcc tgg gca gtt ggc aaa     192
Gly Trp Cys Ile Pro Cys Pro Ile Ile Ile Ala Trp Ala Val Gly Lys
 50                  55                  60 ctc tac tat gag aat gag                                             210
Leu Tyr Tyr Glu Asn Glu
 65                  70

<210> SEQ ID NO 8
<211> LENGTH: 70
<212> TYPE: PRT
<213> ORGANISM: Mus musculus

<400> SEQUENCE: 8

Trp Cys Arg Cys Ile Thr Thr Ile Phe Asn Tyr Phe Val Val Thr Asn
 1               5                  10                  15

Phe Phe Trp Met Phe Val Glu Gly Cys Tyr Leu His Thr Ala Ile Val
             20                  25                  30

Met Thr Tyr Ser Thr Glu His Leu Arg Lys Trp Leu Phe Leu Phe Ile
         35                  40                  45

Gly Trp Cys Ile Pro Cys Pro Ile Ile Ile Ala Trp Ala Val Gly Lys
 50                  55                  60

Leu Tyr Tyr Glu Asn Glu
 65                  70

<210> SEQ ID NO 9
<211> LENGTH: 1374
<212> TYPE: DNA
<213> ORGANISM: Mus musculus
<220> FEATURE:
<221> NAME/KEY: CDS
<222> LOCATION: (79)...(1371)

<400> SEQUENCE: 9
gccggacaga cctcctttgg aagcagccac ttctggtccc catccctgga gcgatcgagc     60
ggcaggatct gctgtccc atg ggg acc cca ggc tct ctt ccc agt gca cag     111
                    Met Gly Thr Pro Gly Ser Leu Pro Ser Ala Gln
                     1               5                  10 ctt ctc ctc tgc ctg ttt tcc ctg ctt cca gtg ctc cag gtg gcc caa     159
Leu Leu Leu Cys Leu Phe Ser Leu Leu Pro Val Leu Gln Val Ala Gln
             15                  20                  25 cca ggc cag gca ccc cag gac cag ccc ctg tgg aca ctt ttg gag cag     207
Pro Gly Gln Ala Pro Gln Asp Gln Pro Leu Trp Thr Leu Leu Glu Gln
         30                  35                  40 tac tgc cac agg acc aca att ggg aat ttt tca ggt ccc tac acc tac     255
Tyr Cys His Arg Thr Thr Ile Gly Asn Phe Ser Gly Pro Tyr Thr Tyr
     45                  50                  55 tgc aac acg acc ttg gac cag atc ggg acc tgt tgg cca cag agc gca     303
Cys Asn Thr Thr Leu Asp Gln Ile Gly Thr Cys Trp Pro Gln Ser Ala
 60                  65                  70                  75 ccc gga gcc cta gta gag aga ccg tgc ccc gag tac ttc aat ggc atc     351
Pro Gly Ala Leu Val Glu Arg Pro Cys Pro Glu Tyr Phe Asn Gly Ile
                 80                  85                  90
```

| | |
|---|---:|
| aag tac aac acg acc cgg aat gcc tac aga gag tgc ctg gag aac ggg<br>Lys Tyr Asn Thr Thr Arg Asn Ala Tyr Arg Glu Cys Leu Glu Asn Gly<br>                                 95                         100                       105 | 399 |
| acc tgg gcc tca agg gtc aac tac tca cac tgc gaa ccc att ttg gat<br>Thr Trp Ala Ser Arg Val Asn Tyr Ser His Cys Glu Pro Ile Leu Asp<br>           110                       115                      120 | 447 |
| gac aag cag aga aag tat gac ctg cat tac cga atc gcc ctc att gtc<br>Asp Lys Gln Arg Lys Tyr Asp Leu His Tyr Arg Ile Ala Leu Ile Val<br>     125                       130                      135 | 495 |
| aac tac ctg ggt cac tgt gtt tcc gtg gtg gcc ctg gtg gcc gct ttc<br>Asn Tyr Leu Gly His Cys Val Ser Val Val Ala Leu Val Ala Ala Phe<br>140                      145                      150                    155 | 543 |
| ctg ctt ttc cta gtg ctg cgg agt atc cgc tgc ctg agg aat gtg atc<br>Leu Leu Phe Leu Val Leu Arg Ser Ile Arg Cys Leu Arg Asn Val Ile<br>                      160                      165                    170 | 591 |
| cac tgg aac ctc atc acc acc ttc att ctg aga aac atc gcg tgg ttc<br>His Trp Asn Leu Ile Thr Thr Phe Ile Leu Arg Asn Ile Ala Trp Phe<br>           175                       180                      185 | 639 |
| ctg ctg caa ctc atc gac cac gaa gtg cac gag ggc aat gag gtc tgg<br>Leu Leu Gln Leu Ile Asp His Glu Val His Glu Gly Asn Glu Val Trp<br>     190                       195                      200 | 687 |
| tgc cgc tgc atc acc acc atc ttc aac tat ttt gtg gtc acc aac ttc<br>Cys Arg Cys Ile Thr Thr Ile Phe Asn Tyr Phe Val Val Thr Asn Phe<br>205                      210                      215 | 735 |
| ttc tgg atg ttt gtg gag ggc tgc tac ctg cac acg gcc att gtc atg<br>Phe Trp Met Phe Val Glu Gly Cys Tyr Leu His Thr Ala Ile Val Met<br>220                      225                      230                    235 | 783 |
| acg tac tcc aca gag cac ctg cgc aag tgg ctt ttc ctc ttc att gga<br>Thr Tyr Ser Thr Glu His Leu Arg Lys Trp Leu Phe Leu Phe Ile Gly<br>                      240                      245                    250 | 831 |
| tgg tgc att ccc tgc cct atc atc atc gcc tgg gca gtt ggc aaa ctc<br>Trp Cys Ile Pro Cys Pro Ile Ile Ile Ala Trp Ala Val Gly Lys Leu<br>     255                       260                      265 | 879 |
| tac tat gag aat gag cag tgc tgg ttt ggc aag gaa gct ggt gat ttg<br>Tyr Tyr Glu Asn Glu Gln Cys Trp Phe Gly Lys Glu Ala Gly Asp Leu<br>          270                       275                    280 | 927 |
| gtg gac tac atc tac cag ggc ccc gtc atg ctt gtg ctg ttg atc aat<br>Val Asp Tyr Ile Tyr Gln Gly Pro Val Met Leu Val Leu Leu Ile Asn<br>285                      290                      295 | 975 |
| ttt gta ttt ctg ttt aac atc gtc agg atc ctg atg acg aag tta cga<br>Phe Val Phe Leu Phe Asn Ile Val Arg Ile Leu Met Thr Lys Leu Arg<br>300                      305                      310                    315 | 1023 |
| gca tcc acc acg tcc gag aca atc caa tac agg aag gca gtg aag gcc<br>Ala Ser Thr Thr Ser Glu Thr Ile Gln Tyr Arg Lys Ala Val Lys Ala<br>                      320                      325                    330 | 1071 |
| acg ctg gtc ctc ctc ccc ctg ttg ggc atc acc tac atg ctc ttc ttt<br>Thr Leu Val Leu Leu Pro Leu Leu Gly Ile Thr Tyr Met Leu Phe Phe<br>          335                       340                      345 | 1119 |
| gtc aat cct ggc gag gac gac ctg tcc cag att gtg ttc atc tac ttc<br>Val Asn Pro Gly Glu Asp Asp Leu Ser Gln Ile Val Phe Ile Tyr Phe<br>     350                       355                      360 | 1167 |
| aac tct ttc ctg cag tcc ttc cag ggt ttc ttt gtg tcc gtt ttc tac<br>Asn Ser Phe Leu Gln Ser Phe Gln Gly Phe Phe Val Ser Val Phe Tyr<br>365                      370                      375 | 1215 |
| tgc ttc ttc aat gga gag gtg cgc gcg gcc ctg aga aag cgg tgg cac<br>Cys Phe Phe Asn Gly Glu Val Arg Ala Ala Leu Arg Lys Arg Trp His<br>380                      385                      390                    395 | 1263 |
| cgc tgg cag gac cac cac gcc ctc cgg gtg cct gtg gcc cgg gcc atg<br>Arg Trp Gln Asp His His Ala Leu Arg Val Pro Val Ala Arg Ala Met | 1311 |

```
                    400              405              410
tcc atc cct acg tcg ccc acc agg atc agc ttc cac agc atc aag cag              1359
Ser Ile Pro Thr Ser Pro Thr Arg Ile Ser Phe His Ser Ile Lys Gln
            415              420              425 aca gct gct gtg tga                                                           1374
Thr Ala Ala Val
        430
```

<210> SEQ ID NO 10
<211> LENGTH: 431
<212> TYPE: PRT
<213> ORGANISM: Mus musculus

<400> SEQUENCE: 10

```
Met Gly Thr Pro Gly Ser Leu Pro Ser Ala Gln Leu Leu Cys Leu
 1               5                  10                  15

Phe Ser Leu Leu Pro Val Leu Gln Val Ala Gln Pro Gly Gln Ala Pro
            20                  25                  30

Gln Asp Gln Pro Leu Trp Thr Leu Leu Glu Gln Tyr Cys His Arg Thr
            35                  40                  45

Thr Ile Gly Asn Phe Ser Gly Pro Tyr Thr Tyr Cys Asn Thr Thr Leu
     50                  55                  60

Asp Gln Ile Gly Thr Cys Trp Pro Gln Ser Ala Pro Gly Ala Leu Val
65                   70                  75                  80

Glu Arg Pro Cys Pro Glu Tyr Phe Asn Gly Ile Lys Tyr Asn Thr Thr
                85                  90                  95

Arg Asn Ala Tyr Arg Glu Cys Leu Glu Asn Gly Thr Trp Ala Ser Arg
            100                 105                 110

Val Asn Tyr Ser His Cys Glu Pro Ile Leu Asp Asp Lys Gln Arg Lys
            115                 120                 125

Tyr Asp Leu His Tyr Arg Ile Ala Leu Ile Val Asn Tyr Leu Gly His
        130                 135                 140

Cys Val Ser Val Val Ala Leu Val Ala Ala Phe Leu Leu Phe Leu Val
145                 150                 155                 160

Leu Arg Ser Ile Arg Cys Leu Arg Asn Val Ile His Trp Asn Leu Ile
                165                 170                 175

Thr Thr Phe Ile Leu Arg Asn Ile Ala Trp Phe Leu Leu Gln Leu Ile
            180                 185                 190

Asp His Glu Val His Glu Gly Asn Glu Val Trp Cys Arg Cys Ile Thr
        195                 200                 205

Thr Ile Phe Asn Tyr Phe Val Val Thr Asn Phe Phe Trp Met Phe Val
    210                 215                 220

Glu Gly Cys Tyr Leu His Thr Ala Ile Val Met Thr Tyr Ser Thr Glu
225                 230                 235                 240

His Leu Arg Lys Trp Leu Phe Leu Phe Ile Gly Trp Cys Ile Pro Cys
                245                 250                 255

Pro Ile Ile Ile Ala Trp Ala Val Gly Lys Leu Tyr Tyr Glu Asn Glu
            260                 265                 270

Gln Cys Trp Phe Gly Lys Glu Ala Gly Asp Leu Val Asp Tyr Ile Tyr
        275                 280                 285

Gln Gly Pro Val Met Leu Val Leu Leu Ile Asn Phe Val Phe Leu Phe
    290                 295                 300

Asn Ile Val Arg Ile Leu Met Thr Lys Leu Arg Ala Ser Thr Thr Ser
305                 310                 315                 320

Glu Thr Ile Gln Tyr Arg Lys Ala Val Lys Ala Thr Leu Val Leu Leu
```

```
                    325                 330                 335
Pro Leu Leu Gly Ile Thr Tyr Met Leu Phe Phe Val Asn Pro Gly Glu
                340                 345                 350

Asp Asp Leu Ser Gln Ile Val Phe Ile Tyr Phe Asn Ser Phe Leu Gln
            355                 360                 365

Ser Phe Gln Gly Phe Val Ser Val Phe Tyr Cys Phe Phe Asn Gly
    370                 375                 380

Glu Val Arg Ala Ala Leu Arg Lys Arg Trp His Arg Trp Gln Asp His
385                 390                 395                 400

His Ala Leu Arg Val Pro Val Ala Arg Ala Met Ser Ile Pro Thr Ser
                405                 410                 415

Pro Thr Arg Ile Ser Phe His Ser Ile Lys Gln Thr Ala Ala Val
            420                 425                 430

<210> SEQ ID NO 11
<211> LENGTH: 23
<212> TYPE: DNA
<213> ORGANISM: Artificial Sequence
<220> FEATURE:
<223> OTHER INFORMATION: "sense" probe for CRF-RB1

<400> SEQUENCE: 11
ctgcatcacc accatcttca act                                               23

<210> SEQ ID NO 12
<211> LENGTH: 20
<212> TYPE: DNA
<213> ORGANISM: Artificial Sequence
<220> FEATURE:
<223> OTHER INFORMATION: "antisense" probe for CRF-RB1

<400> SEQUENCE: 12
agccacttgc gcaggtgctc                                                   20

<210> SEQ ID NO 13
<211> LENGTH: 415
<212> TYPE: PRT
<213> ORGANISM: Mus musucus

<400> SEQUENCE: 13

Met Gly Gln Arg Pro Gln Leu Arg Leu Val Lys Ala Leu Leu Leu
1               5                   10                  15

Gly Leu Asn Pro Val Ser Thr Ser Leu Gln Asp Gln Gln Cys Glu Ser
                20                  25                  30

Leu Ser Leu Ala Ser Asn Val Ser Gly Leu Gln Cys Asn Ala Ser Val
            35                  40                  45

Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Ile Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140
```

-continued

```
Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Val
                165                 170                 175

Ser Pro Glu Val His Gln Ser Asn Val Ala Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Arg Leu Arg Lys Trp Met Phe Val Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
            340                 345                 350

Ser Phe Gln Gly Phe Phe Val Ser Val Phe Tyr Cys Phe Leu Asn Ser
        355                 360                 365

Glu Val Arg Ser Ala Ile Arg Lys Arg Trp Arg Trp Gln Asp Lys
    370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415
```

<210> SEQ ID NO 14
<211> LENGTH: 1582
<212> TYPE: DNA
<213> ORGANISM: Homo sapiens
<220> FEATURE:
<221> NAME/KEY: CDS
<222> LOCATION: (82)...(1413)
<223> OTHER INFORMATION: CRF-R splice-variant insert fragment inserted between nucleotides 516-517 of SEQ ID NO:1.
/note= "This sequence is contained in clone "CRF-R2"."

<400> SEQUENCE: 14

```
cgagcccgca gccgcccgcc ggttcctctg ggatgtccgt aggacccggg cattcaggac      60
ggtagccgag cgagcccgag g atg gga ggg cac ccg cag ctc cgt ctc gtc       111
                        Met Gly Gly His Pro Gln Leu Arg Leu Val
                          1               5                  10 aag gcc ctt ctc ctt ctg ggg ctg aac ccc gtc tct gcc tcc ctc cag      159
Lys Ala Leu Leu Leu Leu Gly Leu Asn Pro Val Ser Ala Ser Leu Gln
              15                  20                  25 gac cag cac tgc gag agc ctg tcc ctg gcc agc aac atc tca gga ctg      207
Asp Gln His Cys Glu Ser Leu Ser Leu Ala Ser Asn Ile Ser Gly Leu
      30                  35                  40
```

```
cag tgc aac gca tcc gtg gac ctc att ggc acc tgc tgg ccc cgc agc    255
Gln Cys Asn Ala Ser Val Asp Leu Ile Gly Thr Cys Trp Pro Arg Ser
         45                  50                  55 cct gcg ggg cag cta gtg gtt cgg ccc tgc cct gcc ttt ttc tat ggt    303
Pro Ala Gly Gln Leu Val Val Arg Pro Cys Pro Ala Phe Phe Tyr Gly
 60                  65                  70 gtc cgc tac aat acc aca aac aat ggc tac cgg gag tgc ctg gcc aat    351
Val Arg Tyr Asn Thr Thr Asn Asn Gly Tyr Arg Glu Cys Leu Ala Asn
 75                  80                  85                  90 ggc agc tgg gcc gcc cgc gtg aat tac tcc gag tgc cag gag atc ctc    399
Gly Ser Trp Ala Ala Arg Val Asn Tyr Ser Glu Cys Gln Glu Ile Leu
                 95                 100                 105 aat gag gag aaa aaa agc aag gtg cac tac cat gtc gca gtc atc atc    447
Asn Glu Glu Lys Lys Ser Lys Val His Tyr His Val Ala Val Ile Ile
            110                 115                 120 aac tac ctg ggc cac tgt atc tcc ctg gtg gcc ctc ctg gtg gcc ttt    495
Asn Tyr Leu Gly His Cys Ile Ser Leu Val Ala Leu Leu Val Ala Phe
                125                 130                 135 gtc ctc ttt ctg cgg ctc agg cca ggc tgc acc cat tgg ggt gac cag    543
Val Leu Phe Leu Arg Leu Arg Pro Gly Cys Thr His Trp Gly Asp Gln
140                 145                 150 gca gat gga gcc ctg gag gtg ggg gct cca tgg agt ggt gcc cca ttt    591
Ala Asp Gly Ala Leu Glu Val Gly Ala Pro Trp Ser Gly Ala Pro Phe
155                 160                 165                 170 cag gtt cga agg agc atc cgg tgc ctg cga aac atc atc cac tgg aac    639
Gln Val Arg Arg Ser Ile Arg Cys Leu Arg Asn Ile Ile His Trp Asn
                175                 180                 185 ctc atc tcc gcc ttc atc ctg cgc aac gcc acc tgg ttc gtg gtc cag    687
Leu Ile Ser Ala Phe Ile Leu Arg Asn Ala Thr Trp Phe Val Val Gln
                190                 195                 200 cta acc atg agc ccc gag gtc cac cag agc aac gtg ggc tgg tgc agg    735
Leu Thr Met Ser Pro Glu Val His Gln Ser Asn Val Gly Trp Cys Arg
            205                 210                 215 ttg gtg aca gcc gcc tac aac tac ttc cat gtg acc aac ttc ttc tgg    783
Leu Val Thr Ala Ala Tyr Asn Tyr Phe His Val Thr Asn Phe Phe Trp
220                 225                 230 atg ttc ggc gag ggc tgc tac ctg cac aca gcc atc gtg ctc acc tac    831
Met Phe Gly Glu Gly Cys Tyr Leu His Thr Ala Ile Val Leu Thr Tyr
235                 240                 245                 250 tcc act gac cgg ctg cgc aaa tgg atg ttc atc tgc att ggc tgg ggt    879
Ser Thr Asp Arg Leu Arg Lys Trp Met Phe Ile Cys Ile Gly Trp Gly
                255                 260                 265 gtg ccc ttc ccc atc att gtg gcc tgg gcc att ggg aag ctg tac tac    927
Val Pro Phe Pro Ile Ile Val Ala Trp Ala Ile Gly Lys Leu Tyr Tyr
                270                 275                 280 gac aat gag aag tgc tgg ttt ggc aaa agg cct ggg gtg tac acc gac    975
Asp Asn Glu Lys Cys Trp Phe Gly Lys Arg Pro Gly Val Tyr Thr Asp
            285                 290                 295 tac atc tac cag ggc ccc atg atc ctg gtc ctg ctg atc aat ttc atc   1023
Tyr Ile Tyr Gln Gly Pro Met Ile Leu Val Leu Leu Ile Asn Phe Ile
300                 305                 310 ttc ctt ttc aac atc gtc cgc atc ctc atg acc aag ctc cgg gca tcc   1071
Phe Leu Phe Asn Ile Val Arg Ile Leu Met Thr Lys Leu Arg Ala Ser
315                 320                 325                 330 acc acg tct gag acc att cag tac agg aag gct gtg aaa gcc act ctg   1119
Thr Thr Ser Glu Thr Ile Gln Tyr Arg Lys Ala Val Lys Ala Thr Leu
                335                 340                 345 gtg ctg ctg ccc ctc ctg ggc atc acc tac atg ctg ttc ttc gtc aat   1167
Val Leu Leu Pro Leu Leu Gly Ile Thr Tyr Met Leu Phe Phe Val Asn
```

```
              350                 355                 360
ccc ggg gag gat gag gtc tcc cgg gtc gtc ttc atc tac ttc aac tcc    1215
Pro Gly Glu Asp Glu Val Ser Arg Val Val Phe Ile Tyr Phe Asn Ser
            365                 370                 375 ttc ctg gaa tcc ttc cag ggc ttc ttt gtg tct gtg ttc tac tgt ttc    1263
Phe Leu Glu Ser Phe Gln Gly Phe Phe Val Ser Val Phe Tyr Cys Phe
        380                 385                 390 ctc aat agt gag gtc cgt tct gcc atc cgg aag agg tgg cac cgg tgg    1311
Leu Asn Ser Glu Val Arg Ser Ala Ile Arg Lys Arg Trp His Arg Trp
395                 400                 405                 410 cag gac aag cac tcg atc cgt gcc cga gtg gcc cgt gcc atg tcc atc    1359
Gln Asp Lys His Ser Ile Arg Ala Arg Val Ala Arg Ala Met Ser Ile
                415                 420                 425 ccc acc tcc cca acc cgt gtc agc ttt cac agc atc aag cag tcc aca    1407
Pro Thr Ser Pro Thr Arg Val Ser Phe His Ser Ile Lys Gln Ser Thr
            430                 435                 440 gca gtc tgagctggca ggtcatggag cagcccccaa agagctgtgg ctgggggat      1463
Ala Val gacggccagg ctccctgacc accctgcctg tggaggtgac ctgttaggtc tcatgccac   1523 tcccccagga gcagctggca ctgacagcct ggggggggccg ctctcccct gcagccgtg   1582

<210> SEQ ID NO 15
<211> LENGTH: 444
<212> TYPE: PRT
<213> ORGANISM: Homo sapiens

<400> SEQUENCE: 15

Met Gly Gly His Pro Gln Leu Arg Leu Val Lys Ala Leu Leu Leu Leu
1               5                   10                  15

Gly Leu Asn Pro Val Ser Ala Ser Leu Gln Asp Gln His Cys Glu Ser
            20                  25                  30

Leu Ser Leu Ala Ser Asn Ile Ser Gly Leu Gln Cys Asn Ala Ser Val
        35                  40                  45

Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140

Arg Pro Gly Cys Thr His Trp Gly Asp Gln Ala Asp Gly Ala Leu Glu
145                 150                 155                 160

Val Gly Ala Pro Trp Ser Gly Ala Pro Phe Gln Val Arg Arg Ser Ile
                165                 170                 175

Arg Cys Leu Arg Asn Ile Ile His Trp Asn Leu Ile Ser Ala Phe Ile
            180                 185                 190

Leu Arg Asn Ala Thr Trp Phe Val Val Gln Leu Thr Met Ser Pro Glu
        195                 200                 205

Val His Gln Ser Asn Val Gly Trp Cys Arg Leu Val Thr Ala Ala Tyr
    210                 215                 220
```

```
-continued

Asn Tyr Phe His Val Thr Asn Phe Phe Trp Met Phe Gly Glu Gly Cys
225                 230                 235                 240

Tyr Leu His Thr Ala Ile Val Leu Thr Tyr Ser Thr Asp Arg Leu Arg
                245                 250                 255

Lys Trp Met Phe Ile Cys Ile Gly Trp Gly Val Pro Phe Pro Ile Ile
            260                 265                 270

Val Ala Trp Ala Ile Gly Lys Leu Tyr Tyr Asp Asn Glu Lys Cys Trp
        275                 280                 285

Phe Gly Lys Arg Pro Gly Val Tyr Thr Asp Tyr Ile Tyr Gln Gly Pro
    290                 295                 300

Met Ile Leu Val Leu Leu Ile Asn Phe Ile Phe Leu Phe Asn Ile Val
305                 310                 315                 320

Arg Ile Leu Met Thr Lys Leu Arg Ala Ser Thr Thr Ser Glu Thr Ile
            325                 330                 335

Gln Tyr Arg Lys Ala Val Lys Ala Thr Leu Val Leu Leu Pro Leu Leu
            340                 345                 350

Gly Ile Thr Tyr Met Leu Phe Phe Val Asn Pro Gly Glu Asp Glu Val
        355                 360                 365

Ser Arg Val Val Phe Ile Tyr Phe Asn Ser Phe Leu Glu Ser Phe Gln
    370                 375                 380

Gly Phe Phe Val Ser Val Phe Tyr Cys Phe Leu Asn Ser Glu Val Arg
385                 390                 395                 400

Ser Ala Ile Arg Lys Arg Trp His Arg Trp Gln Asp Lys His Ser Ile
            405                 410                 415

Arg Ala Arg Val Ala Arg Ala Met Ser Ile Pro Thr Ser Pro Thr Arg
            420                 425                 430

Val Ser Phe His Ser Ile Lys Gln Ser Thr Ala Val
        435                 440
```

CLONING AND RECOMBINANT PRODUCTION OF CRF RECEPTOR(S)

RELATED APPLICATIONS

This is a divisional application under 37 C.F.R. 1.53(b) of pending prior application Ser. No. 09/191,724, filed Nov. 12, 1998, which is, in turn, a continuation-in-part of U.S. Ser. No. 08/483,139, filed Jun. 7, 1995, now abandoned, which is a Divisional of Ser. No. 08/374,009, filed Jan. 17, 1995, which is a continuation-in-part of U.S. Ser. No. 08/353,537, filed Dec. 9, 1994, now abandoned, which is a continuation-in-part of PCT Application No. PCT/US94/05908, filed May 25, 1994, now completed, which is a continuation-in-part of U.S. Ser. No. 08/110,286, filed Aug. 23, 1993, now U.S. Pat No. 5,728,545, which is a continuation-in-part of U.S. Ser. No. 08/079,320, filed Jun. 18, 1993, now abandoned, the entire contents of each of which are hereby incorporated by reference herein.

ACKNOWLEDGEMENT

This invention was made with United States Goverment support under Grant Number DK26745, awarded by the National Institutes of Health. The United States Goverment has certain rights in this invention.

FIELD OF THE INVENTION

The present invention relates to receptor proteins, DNA sequences encoding same, and various uses therefor.

BACKGROUND OF THE INVENTION

Corticotropin-releasing factor (CRF) is a 41-residue hypothalamic peptide which stimulates the secretion and biosynthesis of pituitary adrenocorticotrophic hormone (ACTH) leading to increased adrenal glucocorticoid production. CRF was originally isolated and characterized on the basis of its role in this hypothalamic-pituitary-adrenal axis (HPA) [Vale et al., Science Vol. 213:1394–1397 (1981)]. More recently, however, CRF has been found to be distributed broadly within the central nervous system (CNS) as well as in extra-neural tissues such as the adrenal glands and testes [Swanson et al., Neuroendocrinology Vol. 36:165–186 (1983); Suda et al., J. Clin. Endocrinol. Metab. Vol. 58:919–924 (1984; Fabbri and Dufau, Endocrinology Vol. 127:1541–1543 (1990)], and sites of inflammation, where it may also act as a paracrine regulator or neurotransmitter.

In addition to the critical role of CRF in mediating HPA axis activation, it has been shown to modulate autonomic and behavioral changes that occur during the stress response. Many of these behavioral changes have been shown to occur independently of HPA activation in that they are insensitive to dexamethasone treatment and hypophysectomy [Britton et al., Life Sci. Vol. 38:211–216 (1986); Britton et al., Life Sci. Vol. 39:1281–1286 (1986); Berridge and Dunn, Pharm. Bioch. Behav. Vol. 34:517–519 (1989)]. In addition, direct infusion of CRF into the CNS mimics autonomic and behavioral responses to a variety of stressors [Sutton et al., Nature Vol. 297:331–333 (1982); Brown and Fisher, Brain Res. Vol. 280:75–79 (1983); Stephens et al., Peptides Vol. 9:1067–1070 (1988); Butler et al., J. Neurosci. Vol. 10:176–183 (1990)]. Furthermore, peripheral administration of CRF or the CRF antagonist, a-helical CRF 9-41, failed to affect these changes, thus supporting a direct brain action for CRF in such functions. CRF antagonists given peripherally attenuate stress-mediated increases in ACTH secretion, and when delivered into the cerebral ventricles can mitigate stress induced changes in autonomic activity and behavior.

As a result of the extensive anatomical distribution and multiple biological actions of CRF, this regulatory peptide is believed to be involved in the regulation of numerous biological processes. The peptide has been implicated in the regulation of inflammatory responses. On the one hand, it has been observed, that CRF plays a pro-inflammatory role in certain animal models, while in others CRF can suppress inflammation by reducing injury induced increases in vascular permeability.

It has also been found that CRF can modify steroid production by the gonads, placenta, and adrenal glands. CRF also has vascular effects such as, dilating the superior mesenteric arterial bed and dilating the coronary arteries. In addition to CRF acting on the central nervous system to modify gastrointestinal function, CRF has been found to directly effect the gastrointestinal tract as well.

In order to more fully investigate the role of CRF within the endocrine, gastrointestinal, reproductive, central nervous and immune systems, and the possible interactions of CRF with its cognate receptor, it would be desirable to have available a ready source of CRF receptor. Furthermore, the availability of recombinant receptor would allow the development of less expensive, more sensitive, and automated means for assaying CRF and CRF-like compounds and developing CRF-based therapeutics.

The responsivity to CRF or the quantity of CRF receptors in target tissues has been shown or predicted (from altered sensitivity to CRF) to change in response to a variety of circumstances including Alzheimer's Disease, melancholic depression, anorexia nervosa, Cushing's Disease, alcoholism, and the like. Thus, the development of specific anti-CRF-R antibodies and molecular probes for CRF receptor(s) are desired for use in appropriate diagnostic assays.

BRIEF DESCRIPTION OF THE INVENTION

In accordance with the present invention, there are provided new C-protein-coupled receptor proteins which have high binding affinity for corticotropin-releasing factor (CRF), said proteins are referred to hereinafter as CRF-receptor(s) (CRF-Rs). Invention receptor(s) are principal neuroregulators of the hypothalamic-pituitary-adrenal cortical axis and play an important role in coordinating the endocrine, autonomic and behavioral responses to stress and immune challenge. CRF-Rs are functionally coupled to adenylate cyclase as it transduces the signal for CRF-stimulated intracellular cAMP accumulation. Invention CRF-Rs can be employed in a variety of ways, such as, for example, in bioassays, for production of antibodies thereto, in therapeutic compositions containing such proteins and/or antibodies, and the like.

In accordance with another aspect of the present invention, binding assays employing CRF-Rs are provided, useful for rapidly screening a large number of compounds to determine which compounds (e.g., agonists and antagonists) are capable of binding to the receptors of the invention. The invention binding assays may also be employed to identify new CRF-like ligands (e.g., putative mammalian sauvagine or urotensin). Test samples (e.g., biological fluids) may also be subjected to invention binding assays to detect the presence or absence of CRF or CRF-like compounds.

In accordance with the present invention, recombinant DNA molecules encoding CRF-Rs are also provided. DNA molecules encoding CRF-Rs (or fragments thereof) are useful, for example, as probes for detecting the presence of CRF-R encoding nucleic acids in biological samples, the identification of additional CRF receptor proteins, as coding sequences which can be used for the recombinant expression of the invention receptor proteins (or functional fragments thereof), and the like. Recombinant human CRF-Rs have been expressed in COS cells and bind to CRF and CRF analogs with high affinity. The recombinant production of CRF-Rs makes feasible their use in the foregoing manners. Fragments of CRF-R encoding nucleic acid can also be employed as primers for PCR amplification of CRF-R encoding DNA. In addition, sequences derived from sequences encoding CRF-Rs can also be used in gene therapy applications to target the expression of vectors carrying useful genes to specific cell types.

In accordance with another aspect of the present invention, anti-CRF-R antibodies are also provided CRF-R and anti-CRF-R antibodies are useful for diagnostic assays to determine levels of CRF-Rs in various tissue samples, e.g., neoplastic tissues, and the like. Anti-CRF-R antibodies can also be used to purify CRF-R protein. Moreover, these antibodies are considered therapeutically useful to counteract or supplement the biological effect of CRF-Rs in vivo.

Methods and diagnostic systems for determining the levels of CRF-R in various tissue samples, and levels of CRF-R peptide fragments and CRF in vascular fluid samples, are also provided. These diagnostic methods can be used, for example, for monitoring the level of therapeutically administered CRF-R (or fragments thereof) to facilitate the maintenance of therapeutically effective amounts. These diagnostic methods can also be used to diagnose physiological disorders that result from abnormal levels of CRF or CRF-R.

CRF-Rs, fragments thereof that bind CRF, or analogs thereof, are capable of therapeutically modulating the effect of CRF. For example, CRF-R fragments can inhibit CRF binding to CRF-R and can inhibit CRF-induced ACTH release in vitro by pituitary cells. Thus, CRF-Rs can be administered therapeutically in mammals to reduce high ACTH levels caused by excess CRF. Such treatments can be used, for example, to treat Cushing's Disease, and the like. These CRF-Rs are also useful in combating pituitary tumors that produce CRF. Moreover, they can be used to reduce pituitary ACTH secretion and hence reduce cortisol levels under any condition in which they are abnormally high, such as, for example, during chronic stress, in patients afflicted with anorexia nervosa or alcoholism, and the like. CRF-Rs administered intravenously (IV) are effective to prevent CRF-induced ACTH release. Furthermore, it is contemplated that IV administration of CRF-Rs can reduce intestinal transit time and thus combat irritable bowel syndrome.

BRIEF DESCRIPTION OF THE FIGURES

FIG. 1 presents the results of displacement of $^{125}$I (Nle$^{21}$,Tyr$^{32}$) ovine CRF (OCRF) by r/hCRF, when oCRF is bound to membranes prepared from COSM6 cells transfected with hctCRF receptor (n), or rGnRHR ("), as described in Example 3. The data are from one representative experiment repeated at least four times.

FIGS. 3A and 3B illustrate a sequence comparison of mouse CRF-RB (SEQ ID NO:10) with mouse CRF-RA (SEQ ID NO:13). The alignment was made using the Jotun-Hein method with PAM250 residue weight table. Putative transmembrane domains are indicated with a solid bar above the sequence. Potential glycosylation sites are indicated by an (*).

DETAILED DESCRIPTION OF THE INVENTION

Figure 1:
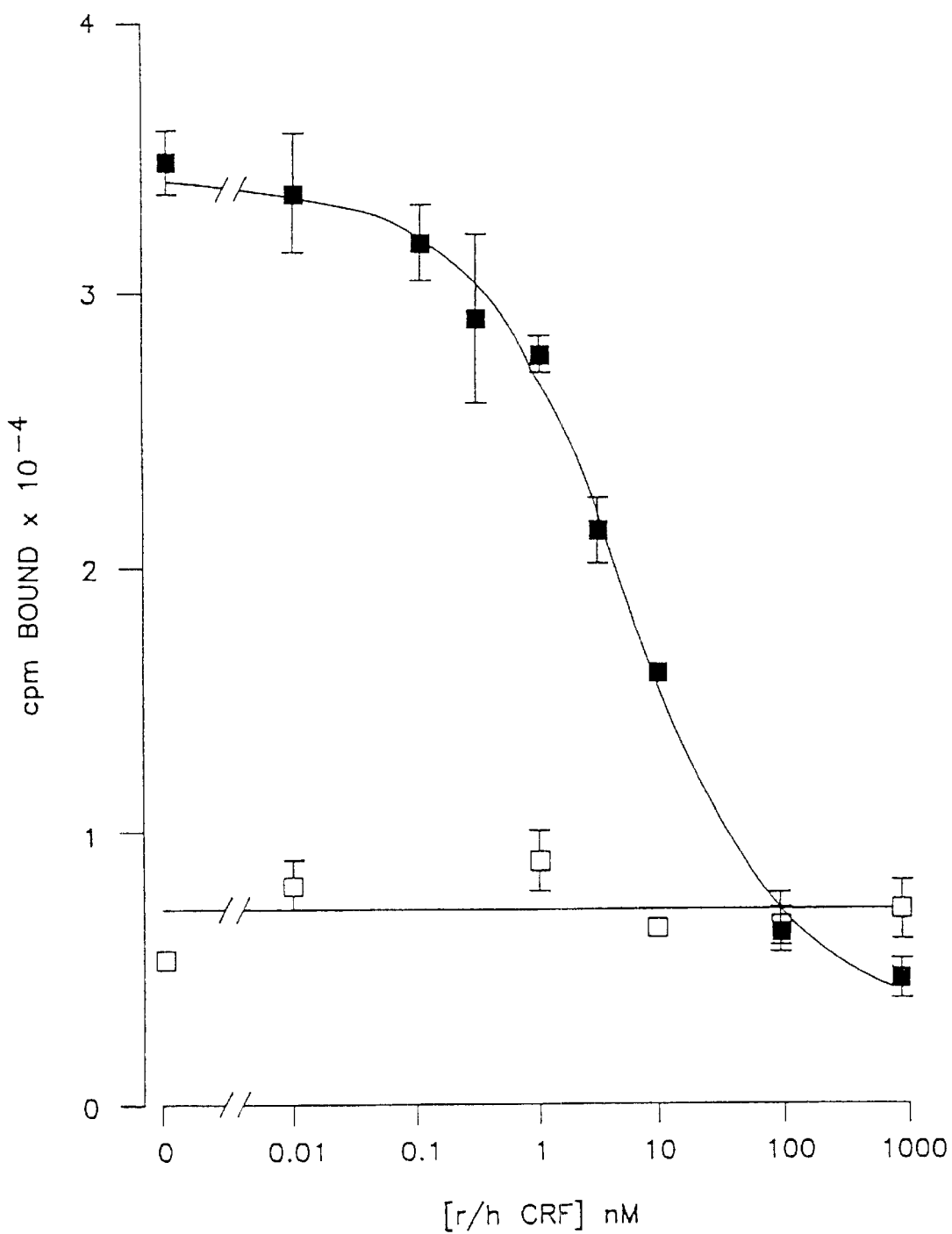
FIG. 1 illustrates the pharmacologic characteristics of plasmid hctCRFR ("human Cushing's Tumor Corticotropin-releasing factor-receptor"; encoding CRF receptor subtype hCRF-RA$_1$), transiently expressed in COSM6 cells.

In accordance with the present invention, there is provided a family of isolated mammalian G-protein-coupled CRF-R proteins characterized as having sufficient binding affinity for CRF and CRF-like ligands such that concentrations of £10 nM of CRF or CRF-like ligands Occupy $^3$ 50% of the binding sites of approximately 0.8 nM of said receptor protein (or approximately 10–20 pmol receptor/mg membrane protein).

Use of the phrase "isolated" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant, isolated and/or substantially pure DNAs, RNAs, polypeptides and proteins of the invention can be produced in large quantities and are useful in ways that the DNAs, RNAS, polypeptides or proteins as they naturally occur are not, such as identification of selective drugs or compounds.

As used herein, "mammalian" refers to the variety of species from which the invention CRF-R protein is derived, e.g., human, rat, mouse, rabbit, monkey, baboon, bovine, porcine, ovine, canine, feline,: and the like. Invention receptors can be derived from a variety of tissue sources, such as, for example, pituitary cells, placental cells, spleen cells, adrenal cells, hematopoietic cells, brain cells, gonadal cells, mesenchymal cells, kidney cells, and the like.

As employed herein, the term "CRF-R" refers to a family of isolated and/or substantially pure receptor protein subtypes which participate in the G-protein-coupled response of cells to CRF and CRF-like ligands. Exemplary CRF peptides include r/h CRF and ovine CRF (see U.S. Pat. No. 4,415,558), and the like. As employed herein, the phrase "CRF-like ligands" includes substances which have a substantial degree of homology (at least 20% homology) with the amino acid sequence of naturally occurring mammalian CRF, as well as alleles, fragments, homologs or derivatives thereof which have substantially the same biological activity as mammalian CRF. Suitable CRF-like ligands can be obtained from a variety of vertebrate species and include such compounds as sauvagine (see, e.g., U.S. Pat. No. 4,605,642), urotensin (see, e.g., U.S. Pat. Nos. 4,908,352; 4,533,654; and 4,525,189) the CRF analogs described in U.S. Pat. Nos: 4,415,558; 4,489,163; 4,594,329; 4,605,642; 5,109,111, each of which are incorporated herein by reference, and the like.

Such receptor subtypes are typically characterized by having seven putative transmembrane domains, preceded by a large extracellular amino-terminal domain and followed by a large intracellular carboxy-terminal domain. Hydropathy analysis of exemplary invention CRF-Rs (described in SEQ ID NOs: 2, 4, 6 and 10) indicates eight hydrophobic regions of approximately 20 amino acids, corresponding to a possible signal peptide at the N-terminus, plus seven putative transmembrane domains. After removal of the signal peptide, an exemplary invention receptor (as described, for example, in SEQ ID NO:2) has a molecular weight of approximately 40–45 kilodaltons.

Exemplary CRF-R amino acid structures are set forth in SEQ ID NOs 2, 4, 6, 8, 10 and 15 of the Sequence Listing provided hereinafter. The CRF-R described in SEQ ID NO:2 contains five potential glycosylation sites at amino acid positions 38, 45, 78, 90 and 98 (and is referred to herein as CRF-RA$_1$). Potential protein kinase C phosphorylation sites are located in the first and second intracellular loops and in the C-terminal tail at positions 146, 222, 386, and 408. Potential casein kinase II and protein kinase A phosphorylation sites are; located at positions 301 and 302, respectively. The third intracellular loop of the invention CRF-R set forth in SEQ ID NO:2 contains an amino acid sequence similar to the Gr activating region found in the third intracellular loop of the b$_2$-adrenergic receptor.

The invention receptor described in SEQ ID NO:2 exhibits appropriate pharmacologic specificity, i.e., having high affinity for human/rat CRF, ovine CRF, the CRF antagonist a helical (9-41) CRF, (DPhe$^{12}$,Nle$^{21,38}$)hCRF(12-41), urotensins, sauvagine, and very low affinity for the biologically impotent analog, [Ala$^{14}$]-OCRF. A series of non-related peptides are inactive, including such compounds as growth hormone releasing factor, salmon calcitonin, vasoactive intestinal polypeptide, and gonadotropin releasing hormone, as shown in FIG. 2C.

Binding affinity (which can be expressed in terms of association constants, Ka, or dissociation constants, K$_d$) refers to the strength of interaction between ligand and receptor, and can be expressed in terms of the concentration of ligand necessary to occupy one-half (50%) of the binding sites of the receptor. A receptor having a high binding affinity for a given ligand will require the presence of very little ligand to become at least 50% bound (hence the K$_d$ value will be a small number); conversely, receptor having a low binding affinity for a given ligand will require the presence of high levels of ligand to become 50% bound (hence the K$_d$ value will be a large number).

Reference to receptor protein "having sufficient binding affinity such that concentrations of CRF less or CRF-like peptides than or equal to 10 nM (i.e., £10 nM) occupy $^3$ 50% (i.e., greater than or equal to one-half) of the binding sites of said receptor protein" means that ligand (i.e., CRF) concentration(s) of no greater than about 10 nM are required in order for the ligand to occupy at least 50% of the active sites of approximately 0.8 nM of said receptor (or approximately 10–20 pmol receptor/mg membrane protein), with much lower ligand concentrations typically being required. Presently preferred receptors are those which have a binding affinity such that ligand concentration(s) in the range of only about 1–10 nM are required in order to occupy (or bind to) at least 50% of the receptor binding sites.

Members of the invention family of receptors can be divided into various subclasses, based on the degree of similarity between specific members. For example, genomic sequences encoding CRF receptors of the same subclass typically have substantially similar restriction maps, while genomic sequences encoding CRF receptors of different subclasses typically have substantially different restriction maps. In addition, sequences encoding members of the same subclass of receptors will hybridize under high stringency conditions, whereas sequences encoding members of different subclasses will hybridize under low stringency hybridization conditions, but not under high stringency hybridization conditions.

Thus, each member of a given subclass is related to other members of the same subclass by having a high degree of homology (e.g., >80% overall amino acid homology) between specific members; whereas members of a given subclass differ from members of a different subclass by having a lower degree of homology (e.g., about 30% up to 80% overall amino acid homology) between specific members of different subclasses.

Based on the above criteria, the receptor species described herein can be designated as CRF-RA or CRF-RB subtypes. Thus, the receptor described in SEQ ID NO:2 is a CRF-RA subtype, and is referred to herein as hCRF-RA$_1$ (for human CRF-R, subtype A, variant 1). The modified form of hCRF-RA$_1$ which contains the insert sequence set forth in SEQ ID NO:4 is referred to herein as hCRF-RA$_2$. Similarly, the receptor described in SEQ ID NO:6 is referred to herein as rCRF-RA (for rat CRF-R, subtype A), and the receptor described in SEQ ID NOs:8 and 10 are referred to herein as mCRF-RB$_1$ (for mouse CRF-R, subtype B, variant 1).

Figure 3A:
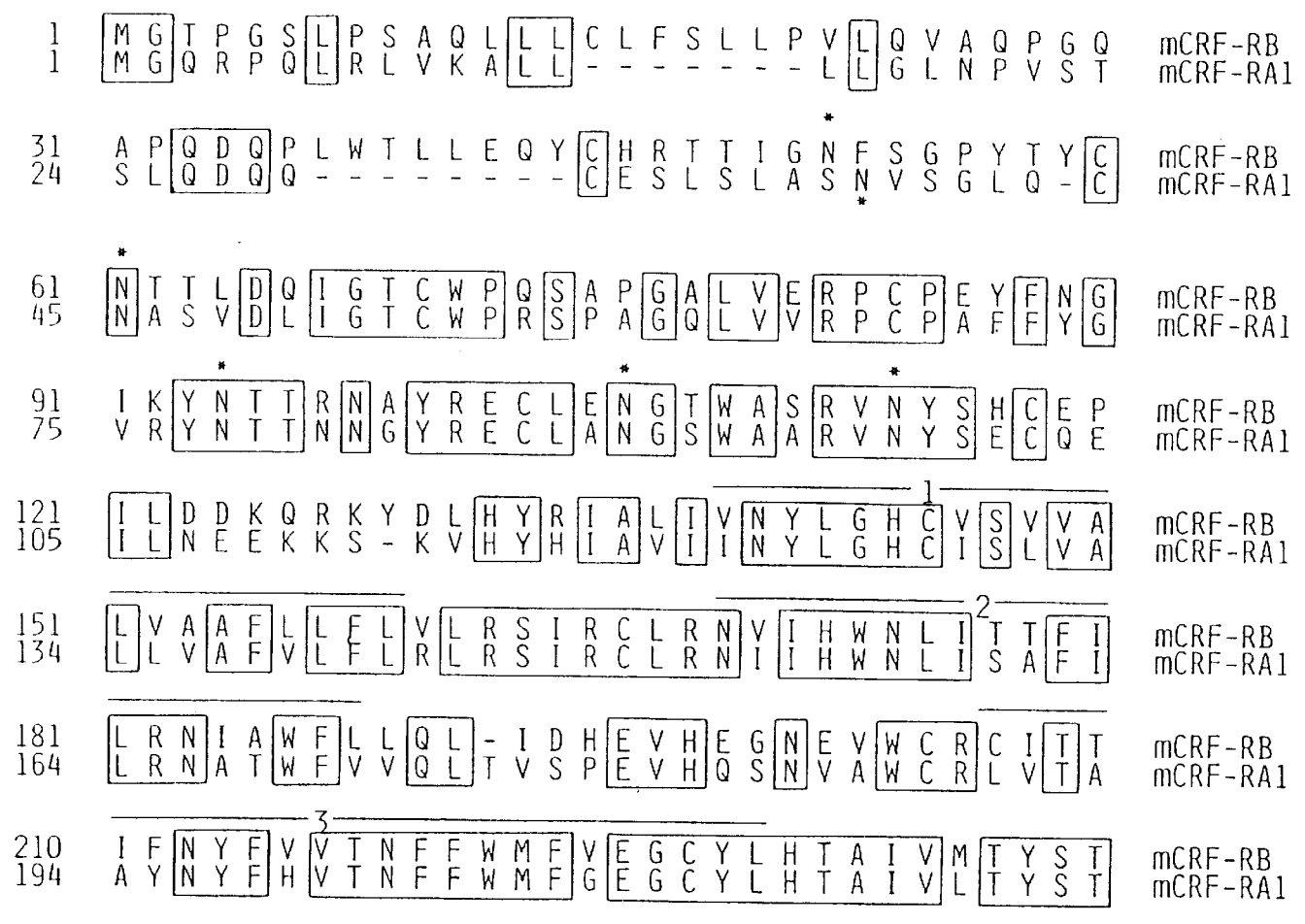
Figure 3B:
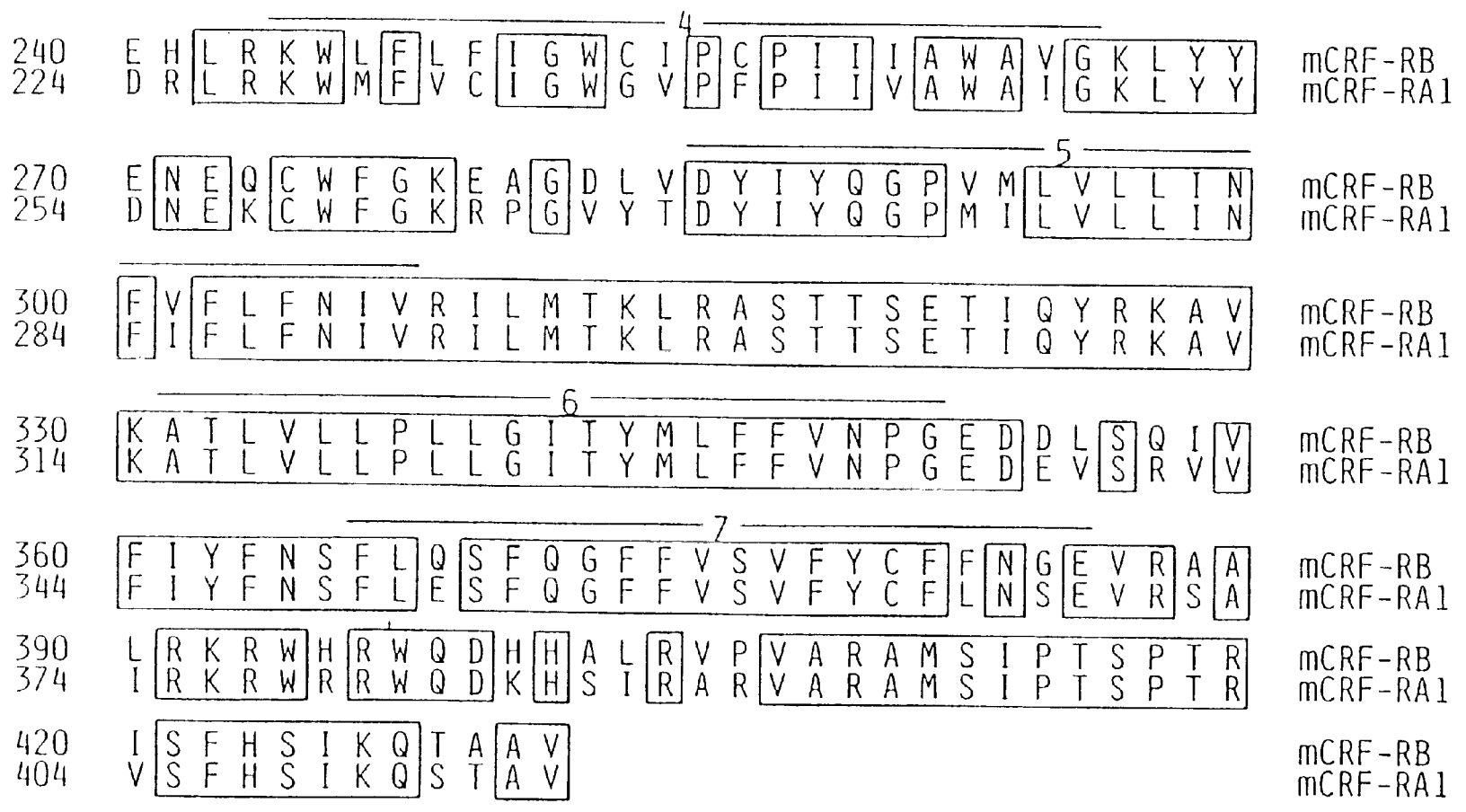

The mouse CRF-RA$_1$ and CRF-RB$_1$ receptors have been compared and are seen to be about 70% homologous at the nucleotide level and 68% homologous at the amino acid level (see, e.g., FIGS. 3A and 3B). In addition, there are a number of fundamental structural characteristics that are conserved between the two receptors. The number and location of potential N-glycosylation sites are the same. Six cysteines are present in the N-terminal domain, characteristic of the receptor family. In the CRF-RB$_1$ receptor, however, there are two additional cysteines, one in the N-terminus and the other at the junction of the first extracellular loop (i.e., ECL-1) and the third transmembrane domain (i.e., TMD-3). If one assumes that the N-terminal cysteine is removed with the signal peptide and that the latter cysteine is within the transmembrane domain, CRF-RB$_1$ is seen to have six cysteines in the extracellular region, as is the case for other members of the receptor family.

The first intracellular loop is practically the same between CRF-RA$_1$ and CRF-RB$_1$, except for the substitution of a valine for the arginine found in CRF-RA$_1$. The second intracellular loop differs in three amino acids, but the changes are conservative. Thus, a methionine, a glutamic acid and a histidine are present in CRF-RB$_1$, instead of a leucine, an aspartic acid and an arginine, respectively, in CRF-RA$_1$. The third intracellular loop is 100% identical between the two receptors. The C-terminal domain is also highly conserved between the two receptors. The putative phosphorylation sites in the intracellular loops are also nearly identical between CRF-RA$_1$ and CRF-RB$_1$, with one exception occurring in the C-terminus, in which SER386 in CRF-RA$_1$ is present as an alanine in CRF-RB$_1$.

A major determinant of the coupling invention CRF-receptors to GTP-binding proteins and subsequently to adenylate cyclase is thought to reside in the third intracellular loop and the C-terminus. Because of the high similarity of the third intracellular loop and the C-termini of CRF-RA$_1$ and CRF-RB$_1$, the coupling and signal transduction properties of the two receptors are expected to be very similar. Indeed, the data (FIG. 5) demonstrate that the signal transduction characteristics of CRF-RA$_1$ and CRF-RB$_1$ are nearly identical. It is expected that a more detailed analysis of the desensitization characteristics of the two receptors will reveal subtle differences as a consequence of the changes in the C-terminus and the other intracellular loops.

The main differences between the two receptors are found in the N-terminal domain, in which sixteen extra amino acids are found in CRF-RB$_1$, and in which there are significant, non-conservative amino acid changes in the remaining portion of the N-terminus. It is interesting to note that, based on the genomic sequence of the mouse CRF-RA$_1$, the amino acid sequences of the two receptors start to diverge very close to the second intron/exon junction in the N-terminus, raising the possibility that some of the divergence between the two receptors could result from alternative exon utilization (i.e., splice variants). Indeed, the presence of multiple protected RNA species when using N-terminal probes is consistent with the existence of splice variants of this receptor.

In addition to the N-terminal domain, the first, second, and third extracellular loops (ECLs-1, -2, and -3) also contain significant differences. For example, extracellular loop-1 in CRF-RB$_1$ contains more charged residues than does the corresponding loop in CRF-RA$_1$. Extracellular loop-2 in CRF-RA$_1$ contains an arginine, instead of a glutamic acid in CRF-RB$_1$. Extracellular loop-3 is the most similar between the two receptors. It is presently believed that a major binding determinant in this family of receptors is the N-terminal region and the extracellular loops. Therefore, the existence of differences in the extracellular domains suggests that the binding specificities between the two receptors should differ. Urotensin ($K_i=0.7\pm0.3$, n=3) and sauvagine ($K_i=0.6\pm0.1$, n=3) show a trend to be more potent than r/hCRF ($K_i=1.3\pm0.2$, n=6) on CRF-RB.

In situ hybridization studies indicate that mRNAs related to CRF-RB have a restricted distribution in the central nervous system that differs considerably from that of CRF-RA. Thus, the receptors derived from the two genes, CRF-RA and CRF-RB, with their distinct tissue distributions and structural diversity especially in the extracellular domains are likely to subserve disparate biological roles.

It is expected that a more detailed pharmacological comparison of the two receptors is likely to reveal significant differences in the binding characteristics of the two receptors. It is also expected that different CRF-R subtypes will mediate different actions of CRF. Thus, by having available nucleic acid encoding various CRF-R subtypes, those of skill in the art have been enabled to screen for and develop selective analogs specific for each CRF-R subtype. The analogs so obtained will be more specific, potent, and effective at binding and modulating the activity of the respective CRF-R subtype.

In one embodiment of the present invention, the CRF-RA$_1$ encoded by the clone referred to herein as "hctCRFR" (described hereinafter) has a high binding affinity for r/h CRF [$K_d=3.3\pm0.45$ nM (n=4)]; ovine CRF [$K_d=2.3\pm0.66$ nM (n=3)]; and for the antagonist a helCRF(9-41) [$K_d=13.0\pm5.2$ nM (n=3)]. This receptor has, a low binding affinity for the biologically impotent analog, [Ala$^{14}$]-ovine CRF [$K_d>300$ nM (n=2)]. In another embodiment of the present invention, the CRF-R described in SEQ ID NO:2 has a binding affinity for r/h CRF of $K_d=3.8\pm0.20$ nM, (n=1).

Presently preferred receptor proteins of the invention have amino acid sequences that are substantially the same as the sequences set forth in Sequence ID Nos. 2, 4, 6, 8, and 10 and amino acid sequences which are substantially the same as the amino acid sequences encoded by the CRF-RA$_1$-encoding portion of clone hctCRFR, deposited with the ATCC under accession number 75474, as well as functional, modified forms thereof. Those of skill in the art recognize that numerous residues of the above-described sequences can be substituted with other, chemically, sterically and/or electronically similar residues without substantially altering the biological activity of the resulting receptor species.

The htcCRFR clone was deposited Jun. 2, 1993, at the American Type Culture Collection (ATCC) 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

As employed herein, the term "substantially the same amino acid sequence" refers to amino acid sequences having at least about 70% identity with respect to the reference amino acid sequence, and retaining comparable functional and biological properties characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred.

Recombinant CRF-R protein can be routinely obtained, employing the invention nucleic acids described hereinafter, having significantly higher purity than naturally occurring CRF-R (e.g., substantially free of other proteins present in crude extracts from mammalian cells). Recombinant DNA techniques well-known in the art, for example, can be used to generate organisms or cell lines that produce heterologous CRF-R protein in significantly higher purities, relative to naturally occurring membrane protein. Subsequently, using appropriate isolation techniques, it is possible to routinely obtain CRF-R proteins which are at least about 70%, preferably 80%, more preferably 90%, and most preferred 98% pure (by weight of total proteins), and which is herein referred to as substantially pure.

In accordance with a further embodiment of the present invention, there is provided a binding assay employing receptors of the invention, whereby a large number of compounds can be rapidly screened to determine which compounds, if any, are capable of binding to the receptors of the invention. Subsequently, more detailed assays can be carried out with initially identified compounds, to further determine whether such compounds act as agonists or antagonists of invention receptors.

Another application of the binding assay of the invention is the assay of test samples (e.g., biological fluids) for the presence or absence of CRF. Thus, for example, serum from a patient displaying symptoms thought to be related to over- or under-production of CRF can be assayed to determine if the observed symptoms are indeed caused by over- or under-production of CRF (or CRF receptor).

The binding assays contemplated by the present invention can be carried out in a variety of ways, as can readily be identified by one of skill in the art. For example, competitive binding assays can be employed, as well as radioimmunoassays, ELISA, ERMA, and the like.

In accordance with a still further embodiment of the present invention, there are provided bioassays for evaluating whether test compounds are capable of acting as agonists or antagonists of receptor(s) of the present invention (or functional modified forms thereof).

Invention CRF-Rs are coupled by heterotrimeric G-proteins to various intracellular enzymes, ion channels, and transporters. The G-proteins associate with invention CRF-R proteins at the intracellular face of the plasma membrane. An agonist binding to CRF-R catalyzes the exchanges of GTP for GDP on the a-subunit (G-protein "activation"), resulting in its dissociation and stimulation of one (or more) of the various signal-transducing enzymes and channels. The different G-protein a-subunits preferentially stimulate particular effectors. The specificity of signal transduction may be determined, therefore, by the specificity of G-protein coupling.

It has been found that invention CRF-R proteins mediate signal transduction through the modulation of adenylate cyclase. For example, when CRF binds to CRF-R, adenylate cyclase causes an elevation in the level of intracellular cAMP. Accordingly, in one embodiment of the present invention, the bioassay for evaluating whether test compounds are capable of acting as agonists or antagonists comprises:
(a) culturing cells containing:
DNA which expresses CRF receptor protein(s) or functional modified forms thereof,
wherein said culturing is carried out in the presence of at least one compound whose ability to modulate signal transduction activity of CRF receptor protein is sought to be determined, and thereafter
(b) monitoring said cells for either an increase or decrease in the level of intracellular cAMP.

Methods well-known in the art that measure intracellular levels of cAMP, or measure cyclase activity, can be employed in binding assays described herein to identify agonists and antagonists of the CRF-R. For example, because activation of some G-protein coupled receptors results in decreases or increases in cAMP, assays that measure intracellular cAMP levels (see, e.g., Example 4) can be used to evaluate recombinant CRF-Rs expressed in mammalian host cells.

As used herein, "ability to modulate signal transduction activity of CRF receptor protein" refers to a compound that has the ability to either induce or inhibit signal transduction activity of the CRF receptor protein.

In another embodiment of the present invention, the bioassay for evaluating whether test compounds are capable of acting as agonists comprises:
(a) culturing cells containing:
DNA which expresses CRF receptor protein(s) or functional modified forms thereof, and
DNA encoding a reporter protein, wherein said DNA is operatively linked to a CRF-R responsive transcription element;
wherein said culturing is carried out in the presence of at least one compound whose ability to induce signal transduction activity of CRF receptor protein is sought to be determined, and thereafter
(b) monitoring said cells for expression of said reporter protein.

In another embodiment of the present invention, the bioassay for evaluating whether test compounds are capable of acting as antagonists for receptor(s) of the invention, or functional modified forms of said receptor(s), comprises:
(a) culturing cells containing:
DNA which expresses CRF receptor protein(s), or functional modified forms thereof, and
DNA encoding a reporter protein, wherein said DNA is operatively linked to a CRF-R responsive transcription element
wherein said culturing is carried out in the presence of:
increasing concentrations of at least one compound whose ability to inhibit signal transduction activity of CRF receptor protein(s) is sought to be determined, and
a fixed concentration of at least one agonist for CRF receptor protein(s), or functional modified forms thereof; and thereafter
(b) monitoring in said cells the level of expression of said reporter protein as a function of the concentration of said compound, thereby indicating the ability of said compound to inhibit signal transduction activity.

In step (a) of the above-described antagonist bioassay, culturing may also be carried out in the presence of:
fixed concentrations of at least one compound whose ability to inhibit signal transduction activity of CRF receptor protein(s) is sought to be determined, and
an increasing concentration of at least one agonist for CRF receptor protein(s), or functional modified forms thereof.

Host cells for functional recombinant expression of CRF-Rs preferably express endogenous or recombinant guanine nucleotide-binding proteins (i.e., G-proteins). G-proteins are a highly conserved family of membrane-associated proteins composed of a, b and g subunits. The a subunit, which binds GDP and GTP, differs in different G-proteins. The attached pair of b and g subunits may or may not be unique; different a chains may be linked to an identical bg pair or to different pairs [Linder and Gilman, Sci. Am. 2:56–65 (1992)]. More than 30 different cDNAs encoding G protein a subunits have been cloned [Simon et al., Science 25:802 (1991)]. At least four different b polypeptide sequences are known [Simon et al., Science 252:802 (1991)]. G-proteins switch between active and inactive states by guanine nucleotide exchange and GTP hydrolysis. Inactive G protein is stimulated by a ligand-activated receptor to exchange GDP for GTP. In the active form, the a subunit, bound to GTP, dissociates from the bg complex, and the subunits then interact specifically with cellular effector molecules to evoke a cellular response. Because different G-proteins can interact with different effector systems (e.g., phospholipase C, adenyl cyclase systems) and different receptors, it is useful to investigate different host cells for expression of different recombinant CRF-R receptor subtypes. Alternatively, host cells can be transfected with G-protein subunit-encoding DNAs for heterologous expression of differing G proteins.

Host cells contemplated for use in the bioassay(s) of the present invention include CV-1 cells, COS cells, and the like; reporter and expression plasmids employed typically also contain the origin of replication of SV-40; and the reporter and expression plasmids employed also typically contain a selectable marker.

As used herein, a "CRF-R responsive transcription element" is any promoter region that is induced, e.g., by the well-known G-protein mediated signal transduction mechanism, to initiate transcription upon the binding of a CRF-R agonist, such as CRF. A preferred CRF-R responsive transcription element is a cAMP responsive transcription element. Cyclic AMP (cAMP) responsive transcription elements employed in the bioassay(s) of the present invention are well-known to those of skill in the art. The cAMP response elements respond to increases in intracellular cAMP by initiating trascription of the DNA molecule (i.e., a reporter gene) operatively linked thereto. An exemplary cAMP response element suitable for use herein is the human DNA b-Polymerase gene promoter (see Mamula et al., *DNA and Cell Bio.*, 11:61–70, 1992).

Reporter proteins suitable for use herein are well known in the art. Host cells can be monitored for the level of expression of a reporter gene encoding a reporter protein in a variety of ways, such as, for example, by photometric means, e.g., by colorimetry (with a colored reporter product such as β-galactosidase), by fluorescence (with a reporter product such as luciferase), by enzyme activity, and the like.

Compounds contemplated for screening in accordance with the invention bioassays include CRF or CRF-like ligands, as well as compounds which bear no particular structural or biological relatedness to CRF. Suitable compounds may be obtained from well-known sources, e.g., from peptide libraries, chemical libraries, bacterial and yeast broths, plants, and the like.

Examples of compounds which bear no particular structural or biological relatedness to CRF, but which are contemplated for screening in accordance with the bioassays of the present invention, include any compound that is an antagonist (i.e., is capable of blocking the action of the invention receptor peptides), or an agonist (i.e., is capable of promoting the action of the invention receptor peptides), such as, for example, alkaloids and other heterocyclic organic compounds, and the like.

As employed herein, the term "non-CRF-like" proteins refers to any organic molecule having essentially no structural similarity with CRF (as defined broadly herein).

Also encompassed by the term CRF-R are the various subtypes thereof (e.g., CRF-RA (such as hCRF-RA$_1$ and hCRF-RA$_2$), CRF-RB$_1$, and the like), as well as polypeptide fragments or analogs thereof. Therefore, a CRF-R contemplated by the present invention can be subject to various changes, substitutions, insertions, and deletions, where such changes provide for certain advantages in its use. For example, a peptide fragment is capable of immunologically mimicking a CRF-R native antigenic epitope or is capable of exhibiting another biological property characteristic of CRF-R, such as, for example, binding to CRF or binding to G-protein(s).

Specific CRF-R residues or regions which are necessary for efficient signal transduction may interact with conserved G-protein motifs. In addition, certain short amino acid stretches of the CRF-R, which are necessary for G-protein coupling, also determine the specificity of the G-protein interactions. Thus, polypeptide fragments of the invention CRF-R are useful in assays or therapeutic methods in which controlled binding to various G-proteins is desired.

The term "analog" includes any polypeptide having an amino acid residue sequence substantially identical to a sequence specifically shown herein in which one or more residues have been conservatively substituted with a functionally similar residue and which displays the ability to mimic CRF-R as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue, provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for praline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the requisite activity is maintained.

When additional residues have been added at either terminus for the purpose of providing a "linker" by which the polypeptides of the invention can be conveniently affixed to a label or solid matrix, or carrier, the linker residues do not form CRF-R epitopes, i.e., are not similar in structure to CRF-R. Labels, solid matrices, and carriers that can be used with the polypeptides of this invention are described hereinbelow.

Amino acid residue linkers include at least one residue up to 40 or more residues (more often they comprise 1 to 10 residues), but do not form CRF-R epitopes. Typical amino acid residues used for linking are tyrosine, cysteine, lysine, glutamic acid and aspartic acid. In addition, a subject polypeptide can differ in sequence, unless otherwise specified, from the natural sequence of CRF-R by modification of the sequence by N-terminal acylation e.g., acetylation or thioglycolic acid amidation, and by C-terminal amidation, e.g., with ammonia, methylamine, and the like.

CRF-R polypeptides of the present invention are capable of inducing antibodies that immunoreact with CRF-R. In view of the well established principle of immunologic cross-reactivity, the present invention therefore contemplates antigenically related variants of the polypeptides. An "antigenically related variant" is a subject polypeptide that is capable of inducing antibody molecules that immunoreact with the CRF-R polypeptides described herein.

CRF-R polypeptides of the present invention can be synthesized by any of the techniques that are known to those skilled in the polypeptide art, including recombinant DNA techniques. Synthetic chemistry techniques, such as solid-phase Merrifield-type synthesis, are preferred for producing polypeptide fragments for reasons of purity, antigenic specificity, freedom from undesired side products, ease of production, and the like. An excellent summary of the many techniques available can be found in J. M. Steward and J. D. Young, "Solid Phase Peptide Synthesis", W.H. Freeman Co., San Francisco, 1969; M. Bodansky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference. See also U.S. Pat. No. 5,055,396, incorporated herein by reference.

CRF-R polypeptides can be used, inter alia, in diagnostic methods and systems according to the present invention to detect the level of CRF-R (or fragments thereof) present in a body sample, to detect the level of CRF in a body sample, or to prepare an inoculum as described herein for the preparation of antibodies that immunoreact with epitopes on CRF-R. CRF-R polypeptides can also be used to bind, detect and purify various intracellular G-proteins and CRF-like receptor agonist/antagonists, such as heterocyclic compounds, and the like. In addition, CRF-R polypeptides can be used in therapeutic methods described herein, e.g., to inhibit the CRF-induced ACTH release and decrease the level of ACTH in a patient.

In accordance with yet another embodiment of the present invention, there are provided antibodies generated against the above-described receptor proteins. Such antibodies can be employed for diagnostic applications, therapeutic applications, and the like. Preferably, for therapeutic applications, the antibodies employed will be monoclonal antibodies.

The above-described antibodies can be prepared employing standard techniques, as are well known to those of skill in the art, using invention receptor proteins, or fragments thereof, as antigens for antibody production. Antibodies of the present invention are typically produced by immunizing a mammal with an inoculum containing a CRF-R protein or fragment thereof thereby inducing the production of antibody molecules having immunospecificity for the immunizing agent.

For example, antibodies raised in rabbits against a synthetic peptide fragment of the invention protein recognize the synthetic peptide and the corresponding invention CRF-R on an equimolar basis, and preferably, are capable of inhibiting the activity of the native protein. Antibodies to CRF-R may be obtained, for example, by immunizing three month old male and female white New Zealand rabbits with a suitable synthetic peptide fragment to which Tyr has been added at the C-terminus in order to couple it, as an antigen, to BSA by a bisdiazotized benzidine (BDB) linkage by reaction for 2 hours at 4° C. The reaction mixture is dialyzed to remove low molecular weight material, and the retentate is frozen in liquid nitrogen and stored at −20° C. Animals are immunized with the equivalent of 1 mg of the peptide antigen according to the procedure of Vaughan et al., *Meth. in Enzymology*, 168:588–617 (1989). At four week intervals, the animals are boosted by injections of 200 mg of the antigen and bled ten to fourteen days later. After the third boost, antiserum is examined for its capacity to bind radio-iodinated antigen peptide prepared by the chloramine-T method and then purified by CMC-ion exchange column chromatography or HPLC. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid-phase immunizing polypeptide. The antibody is contacted with the solid-phase immunizing polypeptide for a period of time sufficient for the polypeptide to immunoreact with the antibody molecules to form a solid-phase immunocomplex. The bound antibodies are separated from the complex by standard techniques.

Antibody so produced can be used, inter alia, in diagnostic methods and systems to detect the level of CRF-R present in a mammalian, preferably human, body sample, such as tissue or vascular fluid. The anti-CRF-R antibodies can also be used for immunoaffinity or affinity chromatography purification of CRF-R biological materials. In addition, an anti-CRF-R antibody according :to the present invention can be used in mammalian therapeutic methods, preferably human, as a CRF-R agonist or antagonist, to neutralize or modulate the effect of CRF-R, increase the level of free CRF (e.g., CRF not bound by CRF-R), increase CRF-induced ACTH release, increase the level of ACTH-induced gluco-corticoids in a patient, and the like.

The proteins of the invention, and the antibodies of the invention, can be administered to a subject employing standard methods, such as, for example, by intraperitoneal, intramuscular, intravenous, or subcutaneous injection, and the like. Implant and transdermal modes of administration are also appropriate. In addition, proteins of the invention can be delivered by transfection with viral or retroviral vectors that encode invention protein. One of skill in the art can readily determine dose forms, treatment regiments, etc, depending on the mode of administration employed.

In accordance with a further embodiment of the present invention, there are provided isolated and purified nucleic acid molecules (e.g., DNA or RNA) which encode the above-described receptor proteins. The nucleic acid molecules described herein are useful for producing invention CRF-R proteins, when such nucleic acids are incorporated into a variety of protein expression systems known to those of skill in the art. In addition, such nucleic acid molecules (or fragments thereof) can be labeled with a readily detectable substituent and used as hybridization probes for assaying for the presence and/or amount of a CRF-R gene or mRNA transcript in ia given sample. Such nucleic acid molecules (or fragments thereof), when labeled with a readily detectable substituent, can also be used as hybridization probes for identifying additional CRF-R genes. The nucleic acid molecules described herein, and fragments thereof, are also useful as primers and/or templates in a PCR reaction for amplifying genes encoding the CRF-R protein described herein. In addition, the nucleic acid molecules described herein, and fragments thereof, are also useful as primers and/or templates in a PCR reaction for identifying genes encoding additional CRF-R proteins which are part of the family of receptor proteins described herein.

The above-described receptor(s) can be encoded by numerous nucleic acid molecules, e.g., a nucleic acid molecule having a contiguous nucleotide sequence substantially the same as:

nucleotides 82–1329 of Sequence ID No. 1, nucleotides 82–1329 of Sequence ID No. 1, further containing nucleotides 1–87 of SEQ ID No. 3 inserted between nucleotides 516–517 of SEQ ID No. 1, nucleotides 81–1324 of Sequence ID No. 5, substantially all nucleotides of Sequence ID No. 7, nucleotides 79–1371 of Sequence ID No. 9, the CRF-RA$_1$-encoding portion of clone hctCRFR, deposited with the ATCC under accession number 75474, or variations thereof which encode the same amino acid sequences, but employ different codons for some of the amino acids, or splice variant cDNA sequences thereof.

As employed herein, the phrase "nucleic acid" refers to ribonucleic acid (RNA) or deoxyribonucleic acid (DNA). DNA can be either complementary DNA (cDNA) or genomic DNA, e.g. a gene encoding a CRF-R.

As employed herein, the phrases "contiguous nucleotide sequence substantially the same as" or "substantially the same nucleotide sequence" refers to DNA having sufficient homology to the reference polynucleotide, such that it will hybridize to the reference nucleotide under typical moderate stringency conditions. In one embodiment, nucleic acid molecules having substantially the same nucleotide sequence as the reference nucleotide sequence encodes substantially the same amino acid sequence as that of any one of SEQ ID NOs:2, 4, 6, 8, or 10. In another embodiment, DNA having "substantially the same nucleotide sequence" as the reference nucleotide sequence has at least 600 homology with respect to the reference nucleotide sequence. DNA having at least 70%, more preferably 80%, yet more preferably 90%, homology to the reference nucleotide sequence is preferred.

Yet other DNAs which encode the above-described receptor are those having a contiguous nucleotide sequence substantially the same as set forth in Sequence ID Nos. 1, 3, 5, 7, or 9 or the CRF-RA$_1$-encoding portion of clone hctCRFR, deposited with the ATCC under accession number 75474.

"Gene(s)" (i.e., genomic DNA) encoding invention CRF-Rs typically contain at least two introns. Thus, alternatively spliced variant cDNA sequences encoding invention CRF-Rs are contemplated herein (e.g., CRF-RA$_2$) For example, SEQ ID NO:3 sets forth an 87 bp cDNA splice variant insert sequence that is inserted between nucleotide positions 516–517 of the CRF-RA$_1$ encoding cDNA set forth in SEQ ID NO:1 (thereby producing CRF-RA$_2$).

As used herein, the phrases "splice variant" or "alternatively spliced", when used to describe a particular nucleotide sequence encoding an invention receptor, refers to a cDNA sequence that results from the well known eukaryotic RNA splicing process. The RNA splicing process involves the removal of introns and the joining of exons from eukaryotic primary RNA transcripts to create mature RNA molecules of the cytoplasm.

Methods of isolating splice variant nucleotide sequences are well known in the art. For example, one of skill in the art can employ nucleotide probes derived from the CRF-R encoding cDNA of SEQ ID NOs 1, 3, 5, 7, or 9 to screen the Cushing's tumor cDNA library described in the Examples or other cDNA libraries derived from cells believed to express CRF-Rs, e.g., brain, heart, pituitary, immune, gonadal, adrenal, placental, gastrointestinal, pulmonary, corticotropic, and the like.

In a preferred embodiment, cDNA encoding CRF-Rs as disclosed herein have substantially the same nucleotide sequence as nucleotides 82–1329 of SEQ ID NO:1, as nucleotides 82–1329 of SEQ ID NO:1 further containing nucleotides 1–87 of SEQ ID NO:3 inserted between nucleotides 516–517 of SEQ ID NO:1, as SEQ ID NO:5, as nucleotides 81–1324 of SEQ ID NO:7, or as nucleotides 79–1371 of SEQ ID NO:9. The presently most preferred cDNA molecules encoding the CRF-Rs have the same nucleotide sequence as nucleotides 82–1329 of SEQ ID NO:1, as nucleotides 82–1329 of SEQ ID NO:1 further containing nucleotides 1–87 of SEQ ID NO:3 inserted between nucleotides 516–517 of SEQ ID NO:1, as SEQ ID NO:5, as nucleotides 81–1324 of SEQ ID NO:7, or as nucleotides 79–1371 of SEQ ID NO:9.

In accordance with another embodiment of the present invention, isolated and purified nucleic acid encoding a CRF-R may be selected from:

(a) DNA encoding the amino acid sequence set forth in SEQ ID NO:2, SEQ ID NO:6, SEQ ID NO:8 or SEQ ID NO:10; or DNA encoding the amino acid sequence set forth in SEQ ID NO:2 further comprising the amino acid sequence set forth in SEQ ID NO:4 inserted between amino acids,145–146 of SEQ ID NO:2, or (b) DNA that hybridizes to the DNA of (a) under moderately stringent conditions, wherein said DNA encodes biologically active CRF-R, or (c) DNA degenerate with respect to either (a) or (b) above, wherein said DNA encodes biologically active CRF-R.

Hybridization refers to the binding of complementary strands of nucleic acid (i.e., sense:antisense strands or probe:target-DNA) to each other through hydrogen bonds, similar to the bonds that naturally occur in chromosal DNA. Stringency levels used to hybridize a given probe with target-DNA can be readily varied by those of skill in the art.

As used herein, the phrase "moderately stringent" hybridization refers to conditions that permit target-DNA to bind a complementary nucleic acid that has about 60%, preferably about 75%, more preferably about 85%, homology to the target DNA; with greater than about 90% homology to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C. Denhart's solution and SSPE (see, e.g., Sambrook et al., *Molecular Cloning, A Laboratory Manual,* Cold Spring Harbor Laboratory Press, 1989) are well known to those of skill in the art as are other suitable hybridization buffers.

The term "functional" or "biologically active", when used herein as a modifier of receptor protein(s) of the present invention, refers to a polypeptide that is able to produce one of the functional characteristics, e.g., antigenicity, exhibited by any of the CRF-Rs described herein. In another embodiment, biologically active means that binding of CRF-like ligands (such as CRF analogs, urotensin, sauvagine, and the like). to said receptor protein(s) modifies the receptor interaction with G-proteins, which in turn affects the levels of intracellular second messengers, preferably cAMP, leading to a variety of physiological effects. Stated another way, "functional" means that a signal is transduced as a consequence of agonist activation of receptor protein(s).

As used herein, the term "degenerate" refers to codons that differ in at least one nucleotide from a reference nucleic acid, e.g., SEQ ID NO:1, but encode the same amino acids as the reference nucleic acid. For example, codons specified by the triplets "UCU", "UCC", "UCA", and "UCG" are degenerate with respect to each other since all four of these codons encode the amino acid serine.

The invention nucleic acids can be produced by a variety of methods well-known in the art, e.g., the methods described in Examples 1 and 5, employing PCR amplification using oligonucleotide primers from various regions of SEQ ID NOs:1, 3, 5, 7, 9 and 14 and the like.

One method employed for isolating and !cloning nucleic acids encoding the receptor(s) of the present invention involves expressing, in mammalian cells, a cDNA library prepared from any cell type thought to respond to CRF (e.g., pituitary cells, placental cells, fibroblast cells, and the like) in a suitable host cell, such as, for example, COSM6 cells. The ability of the resulting mammalian cells to bind a labeled receptor ligand (i.e., a labeled CRF analog) is then determined. Finally, the desired cDNA insert(s) are recovered, based on the ability of a particular cDNA, when expressed in mammalian cells, to induce (or enhance) the binding of labeled receptor ligand to said cell.

Alternatively, DNA libraries may be screened employing an immunological expression assay with an antibody raised against the protein of interest. Screening of the expression library with antibodies raised against the protein of interest may also be used, alone or in conjunction with hybridization probing, to identify or confirm the presence of the sought-after DNA sequences in DNA library clones. Such techniques are taught, for example, in Maniatis et al., *Cold Spring Harbor Laboratory Manual,* Cold Spring Harbor, N.Y. (1982), (hereinafter CSH).

In accordance with a further embodiment of the present invention, optionally labeled receptor-encoding cDNAs, or fragments thereof, can be employed to probe library(ies) (e.g., cDNA, genomic, and the like) for additional nucleotide sequences encoding novel mammalian members of the CRF receptor family. Such screening is initially carried out under low-stringency conditions, which comprise a temperature of less than about 42.5° C., a formamide concentration of less than about 50%, and a moderate to low salt concentration. Presently preferred screening conditions comprise a temperature of about 42.5° C., a formamide concentration of about 20%, and a salt concentration of about 5×standard saline citrate (SSC; 20×SSC contains 3M sodium chloride, 0.3M sodium citrate, pH 7.5). Such conditions will allow the identification of sequences which have a substantial degree of similarity with the probe sequence, without requiring perfect homology for the identification of a stable hybrid. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe.

As used herein, a nucleic acid "probe" is single-stranded DNA or RNA, or analogs thereof, that has a sequence of nucleotides that includes at least 14, preferably at least 20, more preferably at least 50, contiguous bases that are the same as (or the complement of) any 14 or more contiguous bases set forth in any of SEQ ID NOs: 1, 3, 5, 7 or 9 or the CRF-RA$_1$-encoding portion of clone hctCRFR. Preferred regions from which to construct probes include 5' and/or 3' coding sequences, sequences predicted to encode transmembrane domains, sequences predicted to encode cytoplasmic loops, signal sequences, ligand binding sites, and the like. The entire cDNA molecule encoding an invention CRF-R may also be employed as a probe. Probes may be labeled by methods well-known in the art, as described hereinafter, and used in various diagnostic kits.

In accordance with yet another embodiment of the present invention, there is provided a method for the recombinant production of invention receptor(s) by expressing the above-described nucleic acid sequences in suitable host cells. The above-described nucleotide sequences can be incorporated into vectors for further manipulation. As used herein, vector (or plasmid) refers to discrete elements that are used to introduce heterologous DNA (e.g., SEQ ID NOs:1, 3, 5, 7 or 9) into cells for either expression or replication thereof. Selection and use of such vehicles are well within the skill of the artisan.

An expression vector includes elements capable of expressing DNAs that are operatively linked with regulatory sequences (such as promoter regions) that are capable of regulating expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention CRF-Rs in eukaryotic host cells, particularly mammalian cells, include cytomegalovirus (CMV) promoter-containing vectors, SV40 promoter-containing vectors, MMTV LTR promoter-containing vectors, and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.) and the like. Other suitable vectors for transformation of E. coli cells include the pET expression vectors (Novagen, see U.S. Pat. No. 4,952,496), e.g., pET11a, which contains the T7 promoter, T7 terminator, the inducible E. coli lac operator, and the lac repressor gene; and pET 12a–c, which contain the T7 promoter, T7 terminator, and the E. coli ompT secretion signal. Another suitable vector is the pIN-IIIompA2 (see Duffaud et al., *Meth. in Enzymology,* 153:492–507, 1987), which contains the lpp promoter, the lacUV5 promoter operator, the ompA secretion signal, and the lac repressor gene.

Particularly preferred base vectors for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Catalog No. 27-4506-01 from Pharmacia, Piscataway, N.J.), and SV40 promoter-based vectors such as pSVb (Clontech, Palo Alto, Calif.), and the like.

The use of a wide variety of organisms has been described for the recombinant production of proteins or biologically active fragments thereof. One of skill in the art can readily determine suitable hosts (and expression conditions) for use in the recombinant production of the peptides of the present invention. Yeast hosts, bacterial hosts, mammalian hosts, and the like can be employed.

In accordance with another embodiment of the present invention, there are provided "recombinant cells" containing the nucleic acid molecules (i.e., DNA or mRNA) of the present invention (e.g., SEQ ID NOs:1, 3, 5, 7 or 9). Methods of transforming suitable host cells, as well as methods applicable for culturing said cells containing a gene encoding a heterologous protein, are generally known in the art. See, for example, Sambrook et al., *Molecular Cloning: A Laboratory Manual* (2 ed.), Cold Spring Harbor Laboratory Press, Cold Spring Harbor, N.Y., USA (1989).

Exemplary methods of transformation include, e.g., transformation employing plasmids, vilral, or bacterial phage vectors, transfection, electroporation, lipofection, and the like. The heterologous nucleic acid can optionally include sequences which allow for its extrachromosomal maintenance, or said heterologous nucleic acid can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris;* see, e.g., U.S. Pat. Nos. 4,882,279, 4,837,148, 4,929,555 and 4,855,231), mammalian cells (e.g., HEK293, CHO, CV-1, and Ltk cells), insect cells, and the like.

The present invention also provides a diagnostic system, preferably in kit form, for assaying for the presence of CRF-R protein, CRF-R polypeptide fragments or analogs, or CRF peptide in a fluid or tissue s ample. A suitable diagnostic system includes, in an amount sufficient for at least one assay, a CRF-R protein (or polypeptide fragment thereof) and/or a subject antibody as a separately packaged immunochemical reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence or quantity of CRF-R (or more likely a fragment of CRF-R) in a vascular fluid sample, such as blood, plasma, or serum, or in a tissue sample, comprises a package containing at least one CRF-R protein or polypeptide fragment thereof of this invention. In addition, a diagnostic system containing at least one CRF-R (or polypeptide fragment thereof) can be used to detect the level of CRF peptide present in a vascular fluid sample or to detect the presence of an intracellular G-protein.

In another embodiment, a diagnostic system of the present invention for assaying for the presence or amount of CRF-R or fragment or analog thereof in a sample includes an anti-CRF-R antibody composition of this invention.

In yet another embodiment, a diagnostic system of the present invention for assaying for the presence or amount of CRF-R or a CRF-R polypeptide in a sample contains at least one CRF-R (or polypeptide fragment thereof) and an anti-CRF-R antibody composition of this invention.

In preferred embodiments, a diagnostic system of the present invention further includes a label or indicating means capable of signaling the formation of a complex containing a nucleic acid probe, protein, polypeptide, or antibody molecule of the present invention.

Also contemplated are immunohistochemistry diagnostic systems for carrying out post-mortem diagnosis of mammalian tissue samples for the presence of CRF-R, which employ the anti-CRF-R antibodies described herein. For details on such diagnostic systems see, for example, Potter et al., *PNAS,* 89:4192–4296 (1992), incorporated herein by reference.

In yet another embodiment of the present invention, a hybridization histochemistry diagnostic system is provided. This diagnostic system is useful for assaying for the presence or amount of nucleic acid encoding CRF-R (e.g., cDNA or mRNA) in a sample (e.g., vascular fluid or cellular tissue). This diagnostic system employs at least one CRF-R encoding nucleic acid probe of this invention.

The word "complex" as used herein refers to the product of a specific binding reaction such as an antibody:antigen, receptor:ligand, protein:protein, or nucleic-acid-probe:nucleic-acid-target reaction. Exemplary complexes are immunoreaction products and CRF:CRF-R complexes.

As used herein, the terms "label" and "indicating means" in their various grammatical forms refer to single atoms and molecules that are either directly or indirectly involved in the production of a detectable signal. Any label or indicating means can be linked to or incorporated in a nucleic acid probe, an expressed protein, polypeptide fragment, or antibody molecule that is part of an antibody or monoclonal antibody composition of the present invention, or used separately. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethyl-rhodamine isothiocyanate (TRITC), lissamine, rhodamine 8200 sulphonyl chloride (RB-200-SC), and the like. A description of immunofluorescence analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, and the like. In such cases where the principal indicating group is an enzyme, additional reagents are required for the production of a visible signal. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

In another embodiment, radioactive elements are employed as labeling agents. An exemplary radiolabeling agent is a radioactive element that produces gamma ray emissions. Elements which emit gamma rays, such as $^{124}$I, $^{125}$I, $^{126}$I, $^{131}$I and $^{51}$Cr, represent one class of radioactive element indicating groups. Particularly preferred is $^{125}$I. Another group of useful labeling means are those elements such as $^{11}$C, $^{18}$F, $^{15}$O and $^{13}$N which emit positrons. The positrons so emitted produce gamma rays upon encounters with electrons present in the animal's body. Also useful is a beta emitter, such as $^{32}$P, $^{111}$indium or $^{3}$H.

The linking of a label to a substrate, i.e., labeling of nucleic acid probes, antibodies, polyp eptides, and proteins, is well known in the art. For instance, antibody molecules can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules (e.g., anti-Ig antibodies), complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or, reagent. In these embodiments, the labeled specific binding agent is capable of specifically binding the amplifying means when the amplifying means is bound to a reagent'species-containing complex.

The diagnostic kits can be used in an "ELISA" format to detect the quantity of CRF, CRF-R, or CRF:CRF-R complex in a vascular fluid sample such as blood, serum, or plasma or in a mammalian tissue sample. "ELISA" refers to an enzyme-linked immunosorbent Assay that employs an antibody or antigen bound to a solid phase land an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090, 3,850,752; and 4,016,043, which are all incorporated herein by reference.

Thus, in preferred embodiments, CRF-R protein, a CRF-R polypeptide fragment thereof, a polyclonal anti-CRF-R antibody, or a monoclonal anti-CRF-R antibody is affixed to a solid matrix to form a solid support that comprises a package in the subject diagnostic systems. A reagent is typically affixed to a solid matrix by adsorption from aqueous medium, although other modes of affixation applicable to proteins and polypeptides well known to those skilled in the art can be used.

Useful solid matrices are also well known in the art. Such materials are water insoluble and include cross-linked dextran (available from Pharmacia Fine Chemicals; Piscataway, N.J.); agarose; beads of polystyrene about 1 micron to about 5 millimeters in diameter (available from Abbott Laboratories; North Chicago, Ill.); polyvinyl chloride; polystyrene; cross-linked polyacrylamide; nitrocellulose- or nylon-based webs such as sheets, strips or paddles; or tubes, plates, or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials contemplated herein in relation to diagnostic systems are those customarily utilized in diagnostic systems. The term "package" refers to a solid matrix or material such as glass, plastic (e.g., polyethylene, polypropylene and polycarbonate), paper, foil, and the like, capable of holding within fixed limits a diagnostic reagent such as a protein, polypeptide fragment, antibody or monoclonal antibody of the present invention. Thus, for example, a package can be a bottle, vial, plastic or plastic-foil laminated envelope container, or the like, used to contain a diagnostic reagent. Alternatively, the container used can be a microtiter plate well to which microgram quantities of a diagnostic reagent have been operatively affixed, i.e., linked so as to be capable of being immunologically bound by an antibody or polypeptide to be detected.

In normal individuals, the levels of CRF can vary from about 1 to 28 picograms per milliliter of vascular fluid. However, during the last trimester of pregnancy, it has been found that there is a tendency for CRF levels to prematurely increase. It is believed that this increase is associated with pregnancy-induced hypertension. Monitoring the change in the level of CRF could facilitate the prediction of the possibility of premature labor, which can be avoided by appropriate treatment.

Thus, by monitoring the level of CRF, an abnormal increase indicative of a potential pathological problem in pregnancy can be detected at an early: stage. Because normal hypertension is now believed to be either caused (or accompanied by) a higher CRF/"CRF-binding protein" ratio than normal, monitoring the level of CRF facilitates the prediction of particular patients who are predisposed to such diseases, and permits therapeutic intervention—as for example by administering dosages of CRF-R protein or polypeptide fragments thereof. By the administration of CRF-R or fragments thereof to treat such pregnancy related disorders, CRF levels can be returned to normal, thus facilitating the normal growth of the fetus.

The present invention contemplates various immunoassay methods for determining the amount of CRF-R in a biological fluid or tissue sample using a CRF-R, a polypeptide fragment thereof (including immunologic fragments, i.e., fragments capable of generating an immune response, as more fully described in Harlowe and Lane, Antibodies: A Laboratory Manual, p. 76 (Cold Spring Harbor Laboratory, 1988)), an anti-CRF-R polyclonal or monoclonal antibody of this invention as an immunochemical reagent to form an immunoreaction product whose amount relates, either directly or indirectly, to the amount of CRF-R in the sample. Also contemplated are immunoassay methods for determining the amount of CRF peptide in a biological fluid sample using a CRF-R or a polypeptide fragment thereof as a reagent to form a product whose amount relates, either. directly or indirectly, to the amount of CRF in the sample.

Various well-known heterogenous and homogenous protocols, either competitive or noncompetitive, solution-phase or solid-phase, can be employed in performing assay methods of the present invention. Those skilled in the art will understand that there are numerous well known clinical diagnostic chemistry procedures in which an immunochemical reagent of this invention can be used to form an immunoreaction product whose amount relates to the amount of CRF-R or CRF present in a body sample.

In one embodiment, the detection of CRF-R protein or polypeptide fragments in a body sample is utilized as a means to monitor the fate of therapeutically administered CRF-R or polypeptide fragments according to the therapeutic methods disclosed herein.

Also contemplated are immunological assays capable of detecting the formation of immunoreaction product formation without the use of a label. Such methods employ a "detection means", which means are themselves well-known in clinical diagnostic chemistry. Exemplary detection means include biosensing methods based on detecting changes in the reflectivity of a surface, changes in the absorption of an evanescent wave by optical fibers, changes in the propagation of surface acoustical waves, and the like.

The present invention contemplates therapeutic compositions useful for practicing the therapeutic methods described herein. Therapeutic compositions of the present invention contain a physiologically compatible carrier together with a CRF-R protein, CRF-R polypeptide fragment, or anti-CRF-R antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable :salts of the components therein. Pharmaceutically acceptable nontoxic salts include the acid addition salts (formed with the free amino groups of the polypeptide) that are formed with inorganic acids such as, for eexample, hydrochloric acid, hydrobromic acid, perchloric acid, nitric acid, thiocyanic acid, sulfuric acid, phosphoric acid, acetic acid, propionic acid, glycolic acid; lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are .sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As previously indicated, administration of the CRF-Rs or polypeptide fragments thereof is effective to reduce vascular fluid CRF levels or high ACTH levels in mammals caused by excessive CRF, which is referred to herein as "CRF-induced ACTH release." In this manner, the CRF-Rs are useful in treating high cortisol (i.e., glucocorticoids) levels which are associated with hypercortisolemia, Cushing's Disease, alcoholism, anorexia nervosa and similar diseases. Likewise, these CRF-Rs are considered to have utility in combatting pituitary tumors that produce CRF—particularly in maintaining stability in a patient until such a tumor can be surgically removed.

In accordance with the present invention, CRF-RB$_1$ has surprisingly been found to be abundantly expressed in the heart. In the isolated perfused heart, the addition of CRF into the left atrium induces a prolonged dilatory effect on coronary arteries, transiently produces a positive ionotropic effect, and stimulates the secretion of atrial natriuretic peptide (Saitoh et al., Gen. Pharmac. (England) 21:337–342 (1990); and Grunt et al., Horm. Metab. Res. (Germany) 24:56–59 (1992)). The surprising finding of CRF-RB$_1$ expression in the blood vessels of the heart raises the possibility that CRF (or other natural or pharmacologic ligands for this receptor) might regulate cardiac perfusion. Furthermore, it is expected that other vascular beds, such as the superior mesenteric, known to be dilated by CRF and related ligands, will also be found to be regulated by CRF and receptors therefor.

Accordingly, since it is known that CRF has a number of biological effects in the heart, it is contemplated that the CRF-R proteins, fragments thereof, or agonists/antagonists thereof (e.g., anti-CRF-R antibodies), can be effectively used to selectively modulate the action of CRF on the heart, particularly in methods to increase the level of CRF that can act on the heart blood vessels to maintain patency.

In accordance with the present invention, the CRF-RB gene has also been found to be expressed in the gastrointestinal tract, as shown, for example, by the presence of CRF-RB$_1$ mRNA in the submucosal and deeper regions of the duodenum. Accordingly, the CRF-RB$_1$ receptor may mediate some of the direct stimulatory effects of CRF on the GI tract that have been described. For example, CRF acts on the gut in vitro to depolarize myenteric neurons in the small intestine (Hanani and Wood, Eur. J. Pharmacol. (Netherlands) 211:23–27 (1992)). In vivo studies with intravenously administered CRF and CRF antagonists are consistent with a direct effect of CRF to control gastric emptying and intestinal motility (Williams et al., Am. J. Physiol. 253:G582–G586 (1987); Lenz, H. J., Horm. Metab. Res. Suppl. 16:17–23 (1987); and Sheldon et al., Regul. Pept. 28:137–151 (1990)). In addition, CRF immunostaining is present at many levels of the GI tract (Nieuwenhuyzen-Kruseman et al., Lancet 2:1245–1246 (1982); Petrusz et al., Federation Proc. 44:229–235 (1985); and Kawahito et al., Gastroenterology 106:859–865 (1994)).

Thus, CRF-Rs (e.g., CRF-RB), fragments thereof, or agonists/antagonists thereof (e.g., anti-CRF-R antibodies), are contemplated for use in treating gastrointestinal disorders, such as irritable bowel syndrome. In addition, CRF antagonists that are selective for CRF-RB are also contemplated for usef in therapeutic methods to treat irritable bowel syndrome.

In addition, the presence of CRF-RB in the epididymis may enable local communication with spermatozoa, which are reported to possess immunoreactive CRF (Yoon et a., Endocrinology 122:759–761 (1988)). Thus, CRF-Rs are also contemplated for use in treating fertility disorders.

The CRF-R proteins and fragments thereof are also useful to treat abnormalities, such as, for example, preeclampsia (toxemia of pregnancy), which occur during pregnancy; for example, they can be used to reduce pregnancy-induced complications and increased CRF levels which can otherwise result in excessive release of ACTH. In addition, CRF-R proteins or fragments thereof can be administered to sequester CRF from vascular fluid, thereby reducing the ratio of CRF/"CRF-binding protein" present in a patient, wherein it is beneficial to reduce the levels of free CRF (i.e., CRF not bound to CRF-BP) in the vascular fluid sample. CRF-binding protein (CRF-BP) is an extracellular serum protein described in Potter et al., supra. The IV administration of CRF-Rs may also be employed in certain instances to modulate blood pressure and thereby combat hypotension.

Since CRF is a known modulator of the immune system, it is contemplated that the administration of CRF-R protein or fragments thereof may be useful to locally treat, i.e., by direct injection into the affected joint, arthritis and other similar ailments. CRF is known to have a number of biological effects on the pituitary, and accordingly, the CRF-R proteins can be used to modulate the action of CRF on the pituitary. Furthermore, it is well known that CRF has a number of biological effects in the brain; therefore, it is contemplated that the CRF-R proteins can be effectively used to modulate the action of CRF on the brain, particularly with respect to control of appetite, reproduction, growth, anxiety, depression, fever and metabolism, as well as the regulation of blood pressure, heart rate, blood flow, and the like.

Thus, the present invention provides for a method for modulating the action of CRF in mammals comprising administering a therapeutically effective amount of a physiologically acceptable composition containing CRF-R protein or polypeptide fragment of the present invention. In addition, the stimulation of ACTH release by CRF can be enhanced by transfecting the subject with a tissue specific CRF-encoding construct.

In another embodiment, the present invention provides a method for treating a pregnancy-related pathological disorder in mammals comprising administering a therapeutically effective amount of a physiologically acceptable composition containing a CRF-R protein or polypeptide fragment of the present invention, said amount being effective to sequester CRF, thereby producing a CRF/"CRF-binding protein" ratio within the normal range for a pregnant female.

Also, as earlier indicated, the administration of anti-CRF-R antibodies described herein is effective to modulate the biological effect of CRF-Rs when administered in vivo. For example, an anti-CRF-R antibody of this invention can be used in the above-described mammalian therapeutic methods to: neutralize or counteract the effect of CRF-R, increase the level of free CRF (e.g., CRF not bound by CRF-R), decrease CRF-induced ACTH release, or decrease the level of ACTH-induced glucocorticoids in a subject. Because increasing the level of free CRF increases the level of CRF-induced ACTH releases, which increases glucocorticoid production, these therapeutic methods are useful for treating certain physiological conditions where increasing the level of glucocorticoids in a patient's vascular fluid is therapeutically effective, such as conditions of inflammation or Addison's Disease, and the like.

Administration of antibodies for this purpose would be carried out along the lines and in amounts generally known in this art, and more particularly along the lines indicated herein with respect to administration of the protein itself.

As described herein, a therapeutically effective amount is a predetermined amount calculated to achieve the desired effect, e.g., to decrease the amount of CRF, ACTH, or decrease the CRF/"CRF-binding protein" ratio in a patient. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of a CRF-R protein or polypeptide fragment thereof that, when administered in a physiologically acceptable composition, is sufficient to achieve a plasma concentration of from about 0.1 mg/ml to about 100 mg/ml, preferably from about 1.0 mg/ml to about 50 mg/ml, more preferably at least about 2 mg/ml and usually 5 to 10 mg/ml. Antibodies are administered in proportionately appropriate amounts in accordance with known practices in this art.

The level of ACTH present in a patient, particularly in the plasma, can be readily determined by routine clinical analysis. In addition, changes in ACTH levels can be monitored during a treatment regimen to determine the effectiveness of the administered CRF-R protein or polypeptide fragment over time.

Thus, the present therapeutic method provides an in vivo means for decreasing ACTH levels in a subject displaying symptoms of elevated serum ACTH, or is otherwise at medical risk by the presence of serum ACTH, wherein it is beneficial to reduce the levels of ACTH. In addition, the present therapeutic method provides an in vivo means for decreasing ACTH-induced cortisol. levels (e.g., glucocorticoids) in a human patient displaying symptoms of elevated serum cortisol.

Likewise, the level of CRF present in a patient, particularly in the plasma, can be readily determined by the diagnostic methods and kits provided herein and readily manipulated by administering CRF-R, analogs thereof, or anti-CRF-R antibodies.

Thus, the present therapeutic method provides an in vivo means for decreasing the CRF/CRF-BP ratio in a subject displaying symptoms of elevated serum CRF/CRF-BP levels, or is otherwise at medical risk by the presence of an elevated serum CRF/CRF-BP ratio, wherein it is beneficial to reduce the levels of free CRF (i.e., CRF not bound to CRF-BP) in the vascular fluid sample.

CRF-R protein(s) (or functional fragments thereof) should be administered under the guidance of a physician. Pharmaceutical compositions will usually contain the protein in conjunction with a conventional, pharmaceutically-acceptable carrier. For treatment, substantially pure synthetic CRF-R or a nontoxic salt thereof, combined with a pharmaceutically acceptable carrier to form a pharmaceutical composition, is preferably administered parenterally to mammals, including humans, either intravenously, subcutaneously, intramuscularly, percutaneously, e.g. intranasally, or intracerebroventricularly; oral administration is possible with an appropriate carrier.

Therapeutic compositions containing CRF-R polypeptide (s) of this invention are preferably administered intravenously, as by injection of a unit dose, for example. The term "unit dose," when used in reference to a therapeutic composition of the present invention, refers to physically discrete units suitable as unitary dosage for the subject, each unit containing a predetermined quantity of active material calculated to produce the desired therapeutic effect in association with the required diluent, i.e., carrier, or vehicle.

Compositions are administered in a manner compatible with the dosage formulation, and in a therapeutically effective amount. The quantity to be administered depends on the subject to be treated, capacity of the subject's immune system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

As an aid to the administration of effective amounts of a CRF-R polypeptide, a diagnostic method of this invention for detecting a CRF-R polypeptide in the subject's blood is useful to characterize the fate:of the administered therapeutic composition.

It may also be desirable to deliver CRP.-R over prolonged periods of time, for example, for periods of one week to one year from a single administration, and slow release, depot or implant dosage forms may be utilized. For example, a dosage form may contain a pharmaceutically acceptable non-toxic salt of. the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain CRF-R or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

As additional examples of the utility of invention compositions, nucleic acids, receptors and/or antibodies of the invention can be used in such areas as the diagnosis and/or treatment of CRF-dependent tumors, enhancing the survival of brain neurons, inducing abortion in livestock and other domesticated animals, inducing twinning in livestock and other domesticated animals, and so on.

In addition, invention cDNAs described herein encoding CRF-Rs (e.g., CRF-RA and CRF-RB) can be used to isolate genomic clones encoding the respective CRF-R gene. The 5' regulatory region of the isolated CRF-R gene can be sequenced to identify tissue-specific transcription elements (i.e., promoter). The tissue-specific CRF-R promoters obtained are useful to target various genes to cells that normally express CRF-Rs. For example, an adenovirus vector, having DNA encoding a cytotoxic protein and a tissue-specific CRF-R promoter for pituitary corticotropic cells, can be used as means for killing pituitary corticotropic tumor cells.

The invention will now be described in greater detail by reference to the following non-limiting examples.

EXAMPLES

Unless otherwise stated, the present invention was performed using standard procedures, as described, for example in Maniatis et al., *Molecular Cloning. A Laboratory Manual,* Cold Spring Harbor Laboratory Press, Cold Spring Harbor, N.Y., USA (1982); Sambrook et al., *Molecular Cloning. A Laboratory Manual* (2 ed.); Cold Spring Harbor Laboratory Press, Cold Spring Harbor, N.Y., USA (1989); Davis et al., *Basic Methods in Molecular Biology,* Elsevier Science Publishing, Inc., New York, USA (1986); *Methods in Enzymology: Guide to Molecular Cloning Techniques* Vol.152, S. L. Berger and A. R. Kimmerl Eds., Academic Press Inc., San Diego, USA (1987); or Harlowe and Lane, *Antibodies: A Laboratory Manual,* p. 76 (Cold Spring Harbor Laboratory, 1988).

Double-stranded DNA was sequenced by the dideoxy chain termination method using the Sequenase reagents from US Biochemicals. Comparison of DNA sequences to databases was performed using the FASTA program [Pearson and Lipman, Proc. Natl. Acad. Sci. USA 85: 2444–2448 (1988)]. Tyr-ovine CRF used for iodination was purchased from Peninsula.

Example 1

Isolation of cDNA Encoding a Human CRF-R

A cDNA library of approximately $1.5 \times 10^6$ independent clones from human pituitary corticotrope adenoma (Cushing's Tumor) cells was constructed in the mammalian expression vector, pcDNA1, and screened using an expression cloning approach [Gearing et al., EMBO J. 8, 3667–3676 (1989)] based on the ability of single transfected cells to detectably bind labeled $^{125}$I-Tyr-ovine CRF. Binding was assessed by performing the transfections and binding reactions directly on chambered microscope slides, then dipping the slides in photographic emulsion, developing the slides after 3–4 days exposure, and analyzing them under a microscope. The possibility of detecting expressed CRF Binding Protein, CRF-BP, rather than authentic CRF-R, was minimized by the selection of an ovine CRF related tracer known to have high affinity for the receptor but low affinity for CRF-BP. Cells which had been transfected with CRF receptor cDNA, and consequently bound radioactive CRF, were covered with silver grains.

Polyadenylated RNA was prepared from human pituitary corticotrope adenoma cells. Corresponding cDNA was synthesized and ligated into the plasmid vector pcDNA1 using non-palindromic BstXI linkers and used to transform MC1061/P3 cells, yielding a library of approximately 1.5× $10^6$ primary recombinants. The unamplified cDNA library was plated at approximately 5000 clones per 100 mm plate. The cells were then scraped off the plates, frozen in glycerol, and stored at −70° C.

Mini-prep DNA was prepared from each pool of 5,000 clones using the alkaline lysis method [Maniatis et al. Molecular Cloning (Cold Spring Harbor Laboratory (1982)]. Approximately ⅒ of the DNA from a mini-prep (10 ml of 100 ml) was transfected into COSM6 cells, and the cells screened for the capacity to bind iodinated Tyr ovine CRF.

More specifically, 2×$10^5$ COS cells were plated on chambered microscope slides (1 chamber-Nunc) that had been coated with 20 mg/ml poly-D-lysine and allowed to attach for at least 3 hours in DMEM and 10% Fetal Calf Serum (complete medium). Cells were subjected to DEAE-Dextran mediated transfection as follows. 1.5 ml of serum-free Dulbecco's Modified Eagle's medium (DMEM) containing 100 mM chloroquine was added to the cells. DNA was precipitated in 200 ml DMEM/chloroquine containing 500 mg/ml DEAE-Dextran, then added to the cells. The cells were incubated at 37° C. for 4 hours, then the media was removed and the cells were treated with 10% DMSO in HEPES buffered saline for 2 minutes. The 10% DMSO was removed, and fresh complete media was added and the cells assayed for binding 2 days later.

Transfected cells prepared as described above were washed twice with HEPES buffered saline (HDB) containing 0.1% ovalbumin, then incubated for 90 minutes at 22° C. in 0.7 ml HDB, 0.1% ovalbumin containing $10^6$ cpm $^{125}$I-Tyr-ovine CRF (approximately 1 ng, 300 pM). The cells were then washed 3× with cold HDB, 0.1% ovalbumin, and 2× with cold HDB, then fixed for 15 minutes at 22° C. in 2.5% glutaraldehyde/HDB and washed 2× with HDB. The chambers were then peeled off the slides, and the slides dehydrated in 95% ethanol, dried under vacuum, dipped in NTB2 photographic emulsion (Kodak) and exposed in the dark at 4° C. for 3–4 days. Following development of the emulsion, the slides were dehydrated in 95% ethanol, stained with eosin and coverslipped with DPX mountant (Electron Microscopy Sciences). The slides were analyzed under darkfield illumination using a Leitz microscope.

Successive subdivision of a positive pool generated a single clone that demonstrated high affinity CRF binding ($K_d$=3.3±0.45 nM) when present in COSM6 cell membranes. The clone containing sequence encoding CRF- receptor is referred to herein as "hctCRFR" and has been deposited with ATCC under accession number 75474, and the receptor encoded thereby is referred to herein as hCRF-RA$_1$.

A phage lZapII library was also synthesized from the same human Cushing's tumor cDNA described above using NotI/EcoRI adapters. A 1.2 kb PstI fragment in the CRF-R coding region of clone "hctCRFR" was used to screen the lZapII library at high stringency using standard methods. of three positive clones identified, two were sequenced and found to contain full length CRF-R cDNA without introns. The clones are labeled "CRF-R1" (also referred to herein as hCRF-RA$_1$) and "CRF-R2" (also referred to herein as hCRF-RA$_2$), portions of which are set forth in SEQ ID NO:1 and SEQ ID NO:3, respectively. Clone CRF-R1 (i.e., hCRF-RA$_1$) contains a 2584 bp insert with a 1245 bp open reading frame encoding a 415 amino acid CRF-R protein. Clone CRF-R2 (also referred to herein as hCRF-RA$_2$) is an alternatively spliced variant sequence of CRF-R1 (i.e., hCRF-RA$_1$) that has the 29 amino acids set forth in SEQ ID NO:4 inserted between amino acids 145–146 of SEQ ID NO:2.

Example 2

Expression of CRF Receptor mRNA

Using well-known autoradiographic methods for binding labelled CRF to various frozen tissue sections, the native CRF receptor has been detected and shown to vary dynamically in the pituitary and various brain regions in experimental animals and in human beings where it is altered in pathologic conditions including Alzheimer's Disease and severe melancholic depression. Furthermore, receptors have been detected in the periphery in organs such as the adrenal, ovary, placenta, gastrointestinal tract and the red pulp, macrophage rich area of the spleen and in sites of inflammation presumably corresponding to the actions of CRF within those tissues.

A Northern-blot assay was conducted by size-fractionating poly(A)$^+$-RNA (derived from rat brain, rat pituitary, rat heart, and mouse AtT20 corticotropic cells) on a denaturing formaldehyde agarose gel and transferring the RNA to nitrocellulose paper using standard methods. The nitrocellulose paper blot was prehybridized for 15 minutes at 68° C. in QuikHybÔ hybridization solution (Stratagene, La Jolla, Calif.) and 100 mg/ml salmon sperm DNA. Next, the blot was hybridized in the same solution at 68° C. for 30 minutes to a "hctCRFR"-derived randomly primed (Amersham, Arlington Heights, Ill.) 1.3 Kb PstI cDNA fragment that contained the majority of the cDNA region of CRF-R1 (i.e., hCRF-RA$_1$). The blot was washed twice at 21° C. in 2×SSPE and 0.15% Sodium Dodecyl Sulfate (SDS) for 15 minutes. Next, the blot was washed twice at 60° C. in 0.2×SSPE and 0.1% SDS for 30 minutes. An autoradiogram of the nitrocellulose paper blot was developed using standard methods.

The results of the Northern-blot assay revealed the presence of a 2.7 Kb CRF-R mRNA transcript in rat brain, rat, pituitary, and in mouse AtT20 corticotropic cells. CRF-R mRNA was not detected in the heart tissue sample.

Example 3

Pharmacologic Characteristics of hctCRFR Transiently Expressed in COSM6 Cells

Approximately $10^6$ COSM6 cells were transfected with either hctCRFR or rGnRHR (rat gonadotropin releasing hormone receptor) by the DEAE-dextran method and grown in 150 mm tissue culture dishes. Two days after transfection, the cells were washed twice with 1 ml HDB and were detached by incubation for 15 min at room temperature in 0.5 mM EDTA in HDB. After pelleting, the cells were washed twice with HDB, and then homogenized in 5% sucrose (16 ml/150 mm dish). The homogenate was centrifuged at 600×g for 5 minutes, and the resulting supernatant was centrifuged at 40,000×g for 20 minutes. The resulting pellet (containing crude membranes) was resuspended at 1–4 mg/ml in 10° C. sucrose, and used in a competitive radioreceptor assay to measure binding, to the CRF-R as described in Perrin et al., *Endoc.*, 118:1171 (1986).

Membrane homogenates (10–24 mg) were incubated at room temperature for 90 minutes with 100,000 cpm $^{125}$I-(Nle$^{21}$, Tyr$^{32}$)-ovine CRF (1 mg CRF was iodinated by chloramine T oxidation to a specific activity of 2,000 Ci/mmol; iodinated CRF was purified by HPLC) and increasing concentrations of unlabeled rat/human (r/h) CRF. The iodinated CRF and unlabeled r/h CRF were both diluted in 20 mM HEPES, 0.1% BSA, 10% sucrose, 2 mM EGTA to a final, pH 7.5 in a final volume of 200 ml and containing MgSO$_4$ to a final concentration of 10 mM. The reaction was terminated by filtration through GF/C (Whatman) filters, prewetted with 1% BSA, 10 mM HEPES, pH 7.5. The filters were washed 4 times with 1 ml 0.1% BSA, 50 mM Tris, pH 7.5. Filter-bound radioactivity, indicating the presence of CRF-R:$^{125}$I-(Nle$^{21}$, Tyr$^{32}$) -ovine CRF complex, was determined by g-scintillation counting.

The results from an assay for the displacement of $^{125}$I-(Nle$^{21}$, Tyr$^{32}$)-ovine CRF by unlabeled human/rat CRF (r/h CRF) are shown in FIG. 1. The results show that native r/h CRF is able to displace labeled ovine CRF in a dose-dependent manner from cells transfected with hctCRFR, but not from cells transfected with rGnRHR. This indicates that the hctCRFR clone encodes a receptor that displays pharmacologic specificity characteristic of a physiologically relevant CRF-receptor (i.e., CRF-RA$_1$).

Example 4

Assay of CRF-R Mediated Stimulation of Intracellular cAMP Levels

To determine the possible linkage of CRF-R to multiple signaling pathways, the ability of CRF-R to stimulate cAMP formation in CRF-R-expressing COSM6 cells was investigated. To ensure that changes in cAMP levels were not influenced by alterations in 1 cAMP phosphodiesterase, the phosphodiesterase inhibitor 3-isobutyl-1-methylxanthine (IBMX) was added to the medium. COSM6 cells were trypsinized 24 hrs following transfection with either ctCRFR or rGnRHR in 150 mm dishes and were replated in 24-well plates (Costar) and allowed to express the receptors for another 24 hrs in 10% FCS, DMEM.

On the day of the stimulation, the medium was changed to 0.1% FCS, DMEM at least 2 hrs before a 30 minute preincubation with 0.1 mM IBMX or medium. Test ligands (i.e., r/h CRF, sauvagine, salmon calcitonin, Vasoactive intestinal peptide (VIP), growth hormone releasing factor (GRF) were added in 0.1% BSA, 0.1% FCS, DMEM, and stimulation was carried out for 30 minutes at 37° C., 7.5% CO$_2$. The medium was removed and the cells were extracted overnight with 1 ml ice-cold 95% EtOH-0.1M HCl at −20° C. Cyclic AMP (cAMP) levels were determined in duplicate from triplicate wells by RIA kit (Biomedical Technologies, Stoughton, Mass.) following the manufacturer's protocol.

Figure 2A:
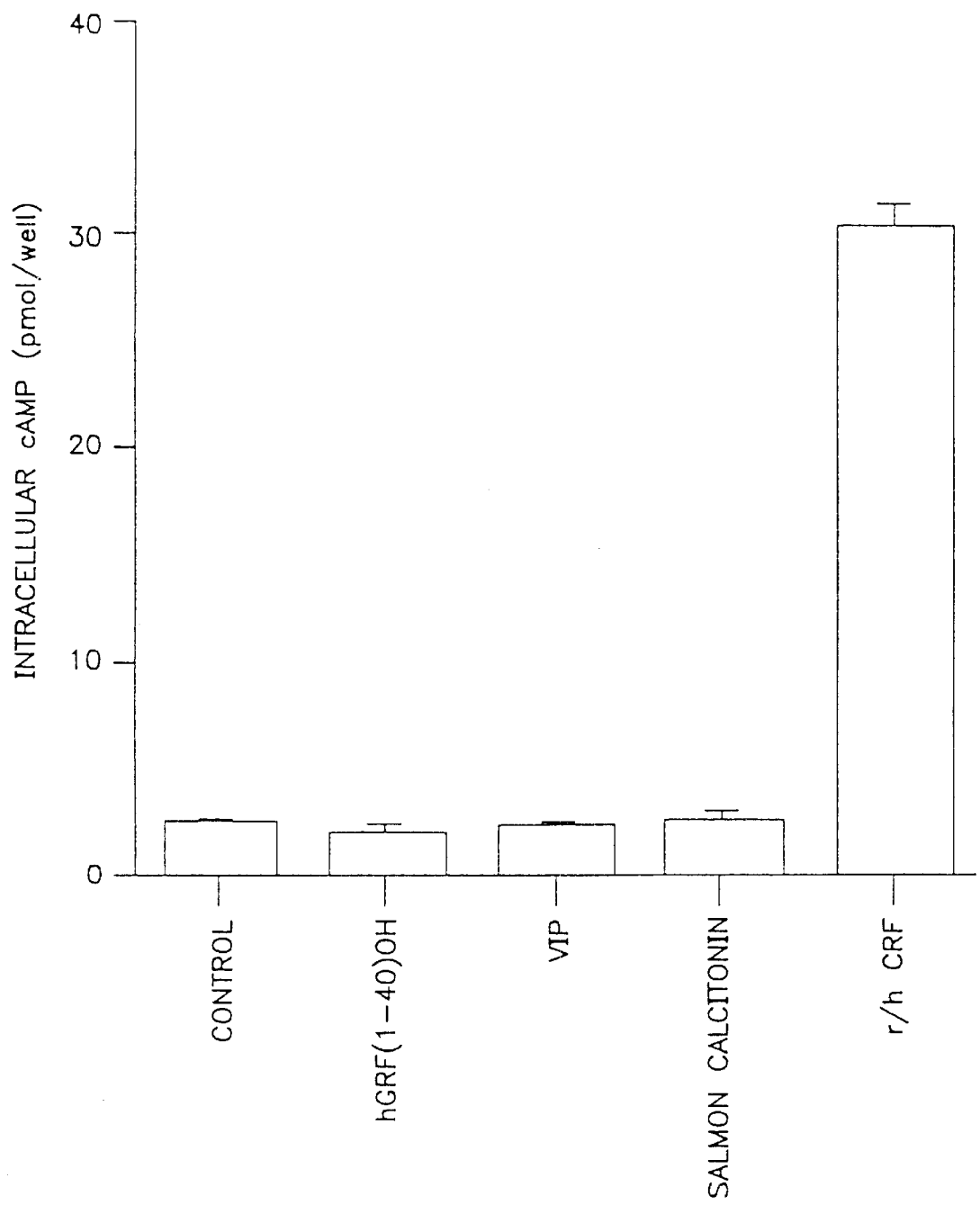
FIG. 2A illustrates the stimulation of intracellular cAMP in COSM6 cells (transfected with plasmid hctCRF, which encodes CRF receptor subtype CRF-RA$_1$) by exposure to CRF, hGRF(1-40)OH, VIP, and Salmon Calcitonin, as described in Example 4.
Figure 2B:
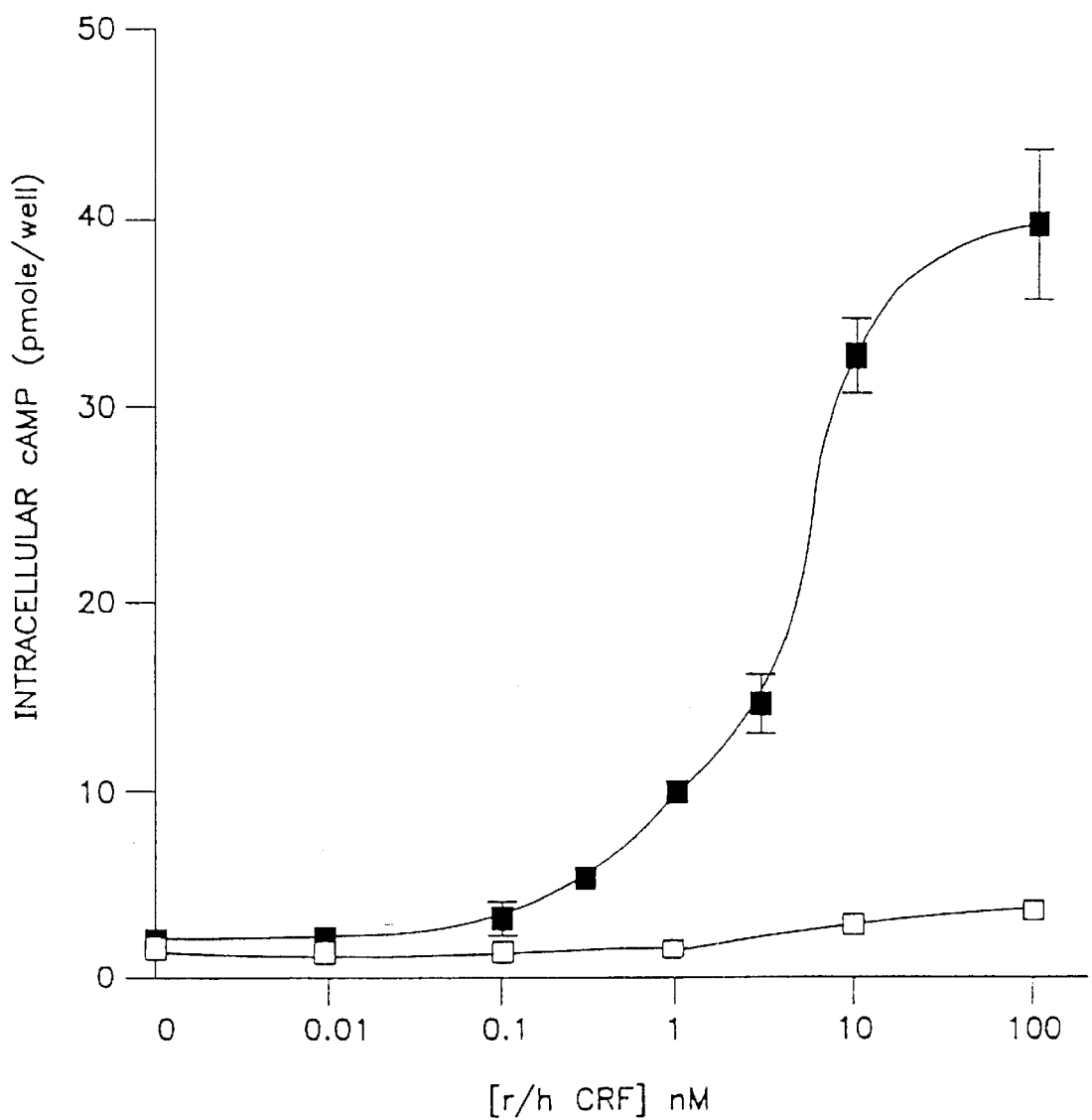
FIG. 2B illustrates the dose-response stimulation of cAMP in COSM6 cells (transfected with plasmid hctCRFR, which encodes CRF receptor subtype CRF-RA$_1$) by increasing concentrations of CRF in cells pretreated (n) or untreated (") with the phosphodiesterase inhibitor, IBMX (3-isobutyl-1-methylxanthine).
Figure 2C:
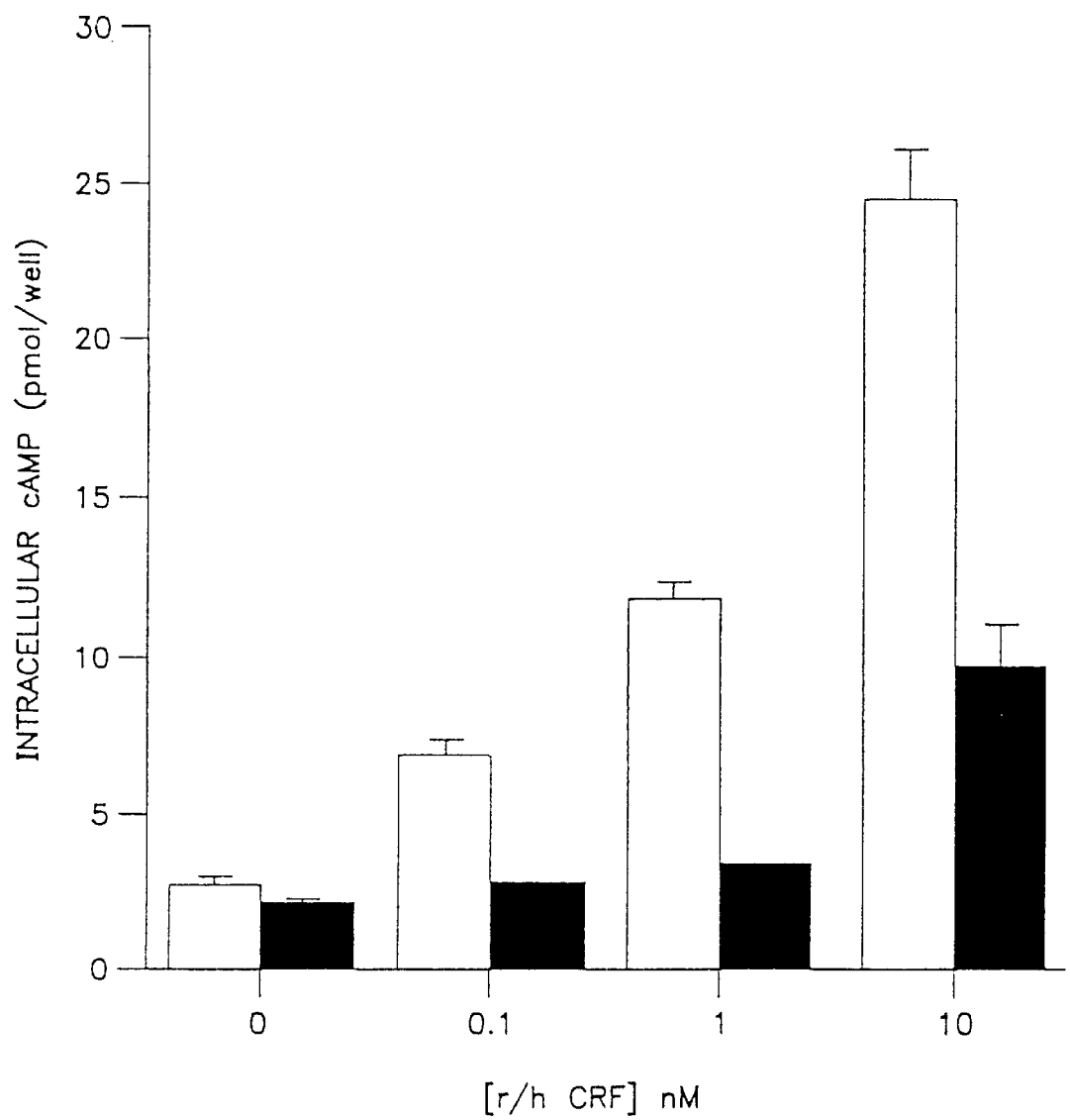
FIG. 2C illustrates the inhibition of CRF stimulated intracellular cAMP by the CRF antagonist a-helical (9-41) CRF. Each determination is taken from a representative experiment performed in triplicate, repeated at least twice. Cells were pretreated with IBMX. Rat/Human (r/h) CRF was added with (solid bars) or without (hollow bars) 2 mM a-helical (9-41).

The results are shown in FIGS. 2A, 2B and 2C. FIGS. 2A and 2B show that COSM6 cells transfected with the cloned hctCRFR respond to CRF with an approximately 10–20 fold increase in intracellular cAMP over basal cAMP levels. Several unrelated peptides have no effect on cyclic AMP levels in the receptor transfected cells. FIG. 2C shows that the CRF antagonist, a helical: (9-41) CRF, blocks the induction of cyclic AMP by r/h CRF.

Example 5

Isolation of cDNA Encoding a Rat CRF-R

Adult Sprague-Dawley rat whole brain poly (A)+RNA was used for the synthesis of a cDNA library. Double-stranded cDNA was ligated to EcoRI-NotI adaptors (Pharmacia/LKB) and cDNAs greater than 2 kilobase pair (kb) were ligated into the lZAPII vector (Stratagene, La Jolla, Calif.). The library was amplified once and approximately 7×10$^5$ clones were screened by hybridization with the 1.2 kb PstI fragment of CRF-R1 (e.g., CRF-RA$_1$) using standard methods. One of the positive clones identified was sequenced and found to contain full length CRF-R cDNA. The positive clone was labeled rat brain CRF-R (rbCRF-RA) and contains an approximate 2500 base pair (bp) insert with a 1245 bp open reading frame encoding a 415 amino acid CRF-R protein. The cDNA and amino acid sequences corresponding to "rbCRF-RA" are set forth in SEQ ID NOs: 5 and 6, respectively.

Example 6

Isolation of Genomic DNA Encoding a Mouse CRF-RB$_1$

Approximately 7×10$^6$ clones of a mouse phage genomic library (obtained from Stratagene, La Jolla, Calif.) were screened by hybridization with a probe comprising nucleotides 204–1402 of rat CRF-RA (see SEQ ID NO:5) using standard methods. Thus, hybridization was carried out in 5×SSPE, 5×Denhardt's solution, and 0.5% SDS for 16 hours at 60° C. The filters were washed twice at room temperature with 2×SSC, 0.1% SDS, then washed twice at 60° C. with 2×SSC, 0.1% SDS.

One of the positive clones identified was sequenced and found to contain an open reading frame encoding a partial CRF-RB$_1$ sequence derived from transmembrane domains 3 through 4 of CRF-RB$_1$. The positive clone was labeled mouse CRF-RB$_1$ (mCRF-RB$_1$) and contains two exons, interrupted by an intron of about 450 nucleotides. The two exons combine to produce a 210 base pair (bp) open reading frame encoding a 70 amino acid portion of a novel CRF-RB$_1$ protein. The cDNA and amino acid sequences corresponding to "mCRF-RB$_1$" are set forth in SEQ ID NOs: 7 and 8, respectively.

Upon further sequencing of clone mCRF-RB$_1$, a third exon was revealed containing an additional 78 base pairs (corresponding to nucleotides 895–972 of SEQ ID NO:9) of an open reading frame encoding the CRF-RB$_1$ protein.

Example 7

Isolation of cDNA Encoding a Mouse CRF-RB$_3$

In order to obtain the cDNA corresponding to the new mouse CRF-RB$_1$ receptor, a mouse heart phage library was screened by hybridization. Approximately 1.2×10$^6$ phage plaques of an amplified oligo-dt primed mouse heart cDNA library in the lambda zap II vector (Stratagene) were screened by hybridization. A probe for the CRF-RB$_1$ cDNA was prepared by PCR using [a$^{32}$P]-dCTP and the following primers:

sense: 5' CTGCATCACCACCATCTTCAACT 3' (SEQ ID NO:11); and
antisense: 5' AGCCACTTGCGCAGGTGCTC 3' (SEQ ID NO:12).

The template used in generating the probe was plasmid DNA corresponding to one exon of CRF-RB$_1$ extending from amino acids 206 to 246 of SEQ ID NO:10. PCR amplification was carried out for 30 cycles (denatured at 94° C. for 1 minute, annealed at 55° C. for 2 minutes and extended at 72° C. for 3 minutes) to yield a 123 bp product corresponding to nucleotides 693–815 of SEQ ID NO:9.

For hybridization screening, the plaques were lifted onto nylon membranes, then denatured, neutralized and rinsed. The membranes were prehyrbridized at 42° C. in 0.6M NaCl, 60 mM sodium citrate, 4×Denhardt's, 40 mM sodium phosphate, pH 6.5, 170 mg/ml salmon sperm DNA, 0.1 SDS, 20% formamide. The membranes were then hybridized at 42° C. in the same solution plus 50% dextran sulfate with approximately 106 cpm of labeled probe per ml of solution. After hybridization, the filters were washed with 0.3M NaCl, 30 mM sodium citrate, 0.1% SDS once at room temperature, twice at 42° C., and twice at 50° C.

A positive plaque was isolated and purified in the next round of plaque hybridization. Helper phage R408 (Biorad) was used for in vivo excision of the lambda zap II clone. The cloned receptor was sequenced on both strands by the dideoxy chain-termination method using the Sequenase kit (United States Biochemical). The clone encoding mouse CRF-RB$_1$ contained a 2.2 kb insert that included a 1293 base pair (bp) open reading frame encoding a protein of 431 amino acids. The full-length CRF-RB$_1$ receptor cDNA was subcloned into the expression vector pcDNAl (Invitrogen) using the EcoRI restriction enzyme to produce the plasmid pCRF-RB$_1$.

Alignments of the nucleotide and amino acid sequences were carried out using the Jotun-Hein weighted method and the PAM250 residue weight table, respectively. CRF-RB$_1$ has 70% homology at the nucleotide level and 686 homology at the amino acid level, to CRF-RA$_1$. FIGS. 3A and 3B present the comparison between the amino acid sequences of CRF-RB$_1$ and CRF-RA$_1$. The alignment was selected to maximize the regions of similarity. There is a putative signal peptide and five putative N-glycosylation sites in the N-terminal domain in CRF-RB$_1$, as there are in CRF-RA$_1$. When comparing CRF-RB$_1$ to CRF-RA$_1$, there is 79% similarity in the seven transmembrane domains (TMD) and 84% similarity in the intracellular loops and the intracellular tail. Yet there is only 60% identity in the extracellular loops (ECL), and 40% identity in the N-terminal domain, which has an additional sixteen amino acids.

All but one of the putative phosphorylation sites in CRF-RA$_1$ are found in CRF-RB$_1$, the missing one being in the C-terminus. CRF-RB$_1$ also has an extra cysteine in a region of the N-terminus which may be within a cleaved putative signal peptide, as well as an extra cysteine at the junction of extracellular loop-1 and transmembrane domain-3, so that the residue may fall within this transmembrane domain.

Example 8

Pharmacologic Characteristics of CRF-RB$_1$ Transiently Expressed in COSM6 Cells Using the methods described in Example 3, a radioreceptor assay was conducted. Approximately 10 mg of PCRF-RB$_1$ plasmid DNA was transfected into COSM6 cells using the DEAE dextran method. Two days later, the cells were detached and crude membrane fractions were prepared and used to measure binding by competitive displacement of $^{125}$I-(Nle$^{21}$,Tyr$^{32}$)-ovine CRF. In order to calculate a K$_d$, the displacement data were analyzed using the, Ligand program of Munson and Rodbard (1980), Anal. Biochem., 107:220–239.

Figure 4:
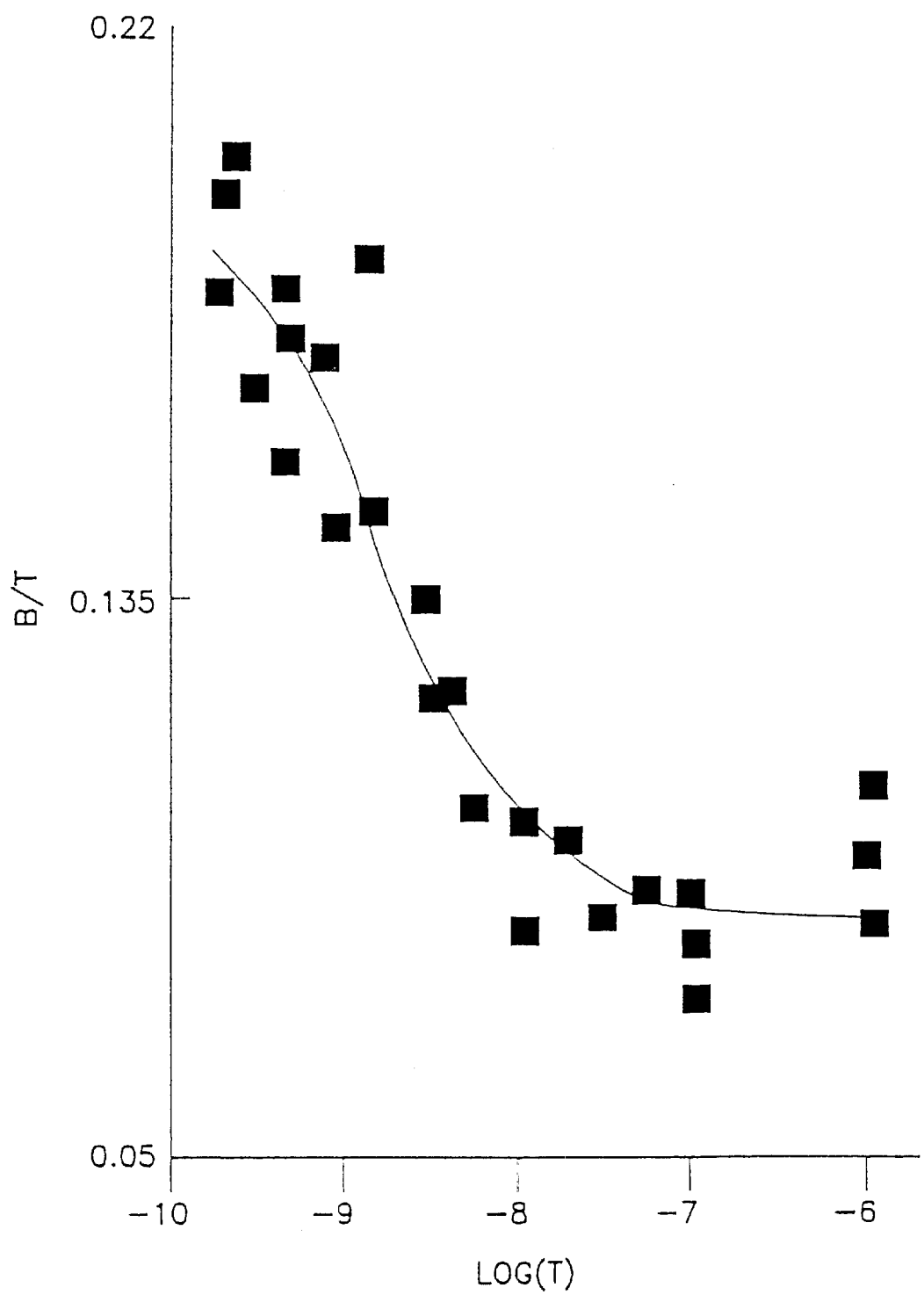
FIG. 4 illustrates results from a competitive displacement of $^{125}$I-(Nle21,Tyr32)-ovine CRF bound to membranes from COSM6 cells transfected with CRF-RB$_1$. "T" indicates "total hormone" and "B" indicates "bound hormone." The data are pooled from three independent experiments.

The cloned CRF-RB$_1$ binds CRF with high affinity as determined by the competitive displacement of bound radioligand. From six experiments, the dissociation constant was determined to be approximately K$_d$=1.3±0.2 nM (see FIG. 4). The binding is specific because the peptides GRF and VIP do not displace the bound radioligand. In addition, the CRF-Rs have high affinity for sauvagine, urotensin, and potent CRF antagonists, such as [DPhe$^{12}$, Nle$^{21,38}$]-hcRF (9-41).

Example 9

Assay of CRF-RB$_1$ Mediated Stimulation of Intracellular cAMP Levels

Using methods described in Example 4, the ability of CRF-RB$_1$ to stimulate cAMP formation in CRF-RB$_1$-expressing COSM6 cells was investigated. The plasmid pCRF-RB$_1$ was transfected into COSM6 cells. One day later, the cells were trypsinized and replated in 10% FBS, DMEM into 24 or 48 well COSTAR tissue culture wells, and allowed to grow another 24 hours. The medium was changed to 0.1% FBS, DMEM at least two hours before treatments. The cells were preincubated for 30 minutes with 0.1 mM 3-isobutyl-1-methylxanthine and then exposed to various peptides for 30 minutes at 37° C. Intracellular cAMP was measured in duplicate from triplicate wells using an RIA kit (Biomedical Technologies, Stoughton, Mass.).

Figure 5:
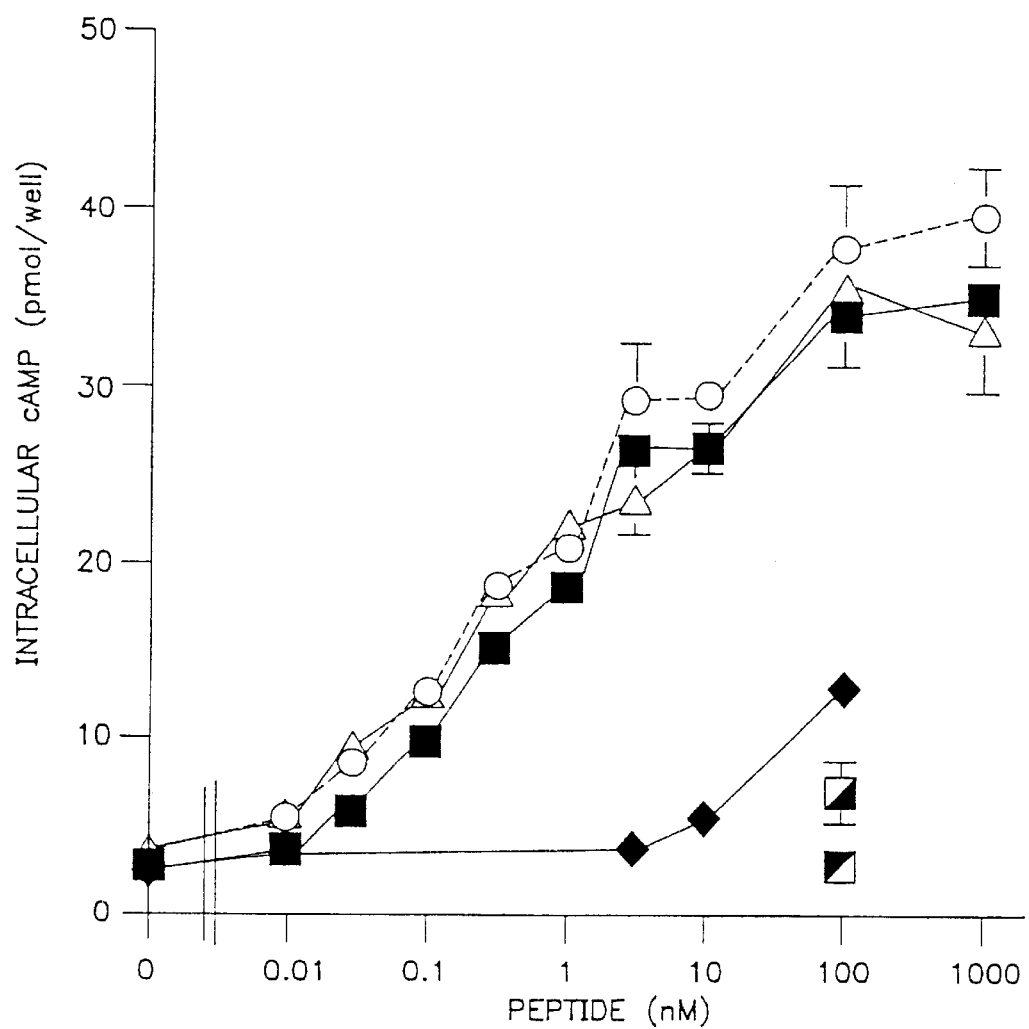
FIG. 5 illustrates the accumulation of intracellular cAMP in COSM6 cells transfected with pCRF-RB$_1$ stimulated by r/hCRF (n), sauvagine (O), suckerfish urotensin (_), hGRF (1-40) OH (o), and VIP (o). Data are also shown for the inhibition of stimulation when the cells are exposed to 1 mM antagonist (DPhe$^{12}$,Nle$^{21,38}$)hCRF(12-41) (t). The data are from one representative experiment described in Example 9, repeated at least twice. The error bars represent the SEM and are smaller than the symbols if not visible.

The results are presented in FIG. 5. The results indicate that CRF stimulates the accumulation of intracellular cAMP when CRF-RB$_1$ is transiently transfected into COSM6 cells. The ECro occurs between 1–10 nM, and the dose response is similar to that seen when the mouse analog of CRF-RA$_1$ is transfected. Urotensin and sauvagine, which are members of the CRF peptide family, are equipotent to CRF in stimulating intracellular cAMP accumulation. The peptides GRF and VIP do not stimulate cAMP accumulation (see FIG. 5). The CRF signal transduced by the cloned CRF-RB$_1$ receptor is inhibited in the presence of 1 mM CRF antagonist, (DPhe$^{12}$,Nle$^{21,38}$)hCRF(12-41).

Example 10

RNase Protection Assay to Determine Tissue Distribution of CRF-RB$_1$

The coding region for mouse receptor corresponding to CRF-RA$_1$ was cloned by the well-known RT-PCR method using primers based on the published sequence, and RNA from mouse AtT-20 cells (ATCC No. CCl 89) as template. Plasmid DNAs encoding amino acids 26–106 of mouse CRF-RA$_1$ (SEQ ID NO:13) and amino acids 1 to 132 of mouse CRF-RB$_1$ (i.e., amino acids 1–132 of SEQ ID NO:9) were linearized, and antisense riboprobes were synthesized using SP6 RNA polymerase and [a-$^{32}$P]Up An internal loading control antisense riboprobe of glyceraldehyde 3-phosphate dehydrogenase (GAPDH) was synthesized using T7 RNA polymerase.

RNase protection assays were performed by hybridizing 30 mg of total RNA from mouse heart and brain tissues to 5×10$^5$ cmp of labeled riboprobe at 65° C. for 18 hours. This was followed by RNase digestion (180 mg/ml RNase A and 350 U/ml RNase T1) at 23° C. for 60 minutes, after which samples were run on 5% polyacrylamide, 8 M urea gels.

RNase protection analysis was used to investigate the relative expression of CRF-RA$_1$ and CRF-RB$_1$ in mouse brain and heart. Whereas both receptors are detected in the brain and the heart, the heart appears primarily to express CRF-RB$_1$ (which has also been reported to express CRF mRNA). There are multiple protected fragments seen in the heart. Furthermore, using a 5' CRF-RB$_1$ probe, the major protected fragment in the brain is smaller than in the heart, and smaller than that expected to be generated from the cloned CRF-RB$_1$.

Example 11

In-situ Hybridization Assay to Determine Tissue Distribution of CRF-RB$_1$

The tissue distribution of CRF-RB$_1$ mRNA was further characterized by in situ hybridization histochemistry using Slabeled antisense cRNA probes. Six week old male C57BL/6 mice were perfused transcardially with 4% paraformaldehyde in 0.1M borate buffer, and regularly spaced series of 20–30 mm thick frozen sections through brain, heart, duodenum and testis/epididymis were taken as described (Simmons et al., J. Histotechnology 12:169–181 (1989)). Radiolabeled antisense and sense (control) cRNA copies were synthesized from a 1.0 kb BamHl digest of CRF-RB$_1$ cDNA, encompassing 80 bp of the 5' untranslated region and 926 bp of the CRF-RB$_1$ coding sequence, subcloned into pBluescript KS vector (Stratagene, La Jolla, Calif.). $^{32}$S-UTP was used as the radioactive isotope for probe synthesis, and in situ hybridization was performed as previously described (Simmons et al., supra; and Imaki et al., Brain Res. 496:35–44 (1989)). Probes were labeled to specific activities of 1–3×10$^9$ dpm/mg, and hybridization was carried out under high stringency conditions (50% formamide with final washes in 0.2×SSC at 70° C.).

Sense-strand cRNAs labeled to similar specific activities failed to show any suggestion of positive localizations when applied to tissue sections adjoining those in which antisense probes revealed robust signals. Consistent with cloning and RNase protection assay data, CRF-RB$_1$ transcripts were detected in the heart, where labeling appeared most prominently over perivascular cells, as well as in the epicardium. In the male reproductive tract, CRF-RB$_1$ mRNA was localized principally in stromal tissue of the epididymis, while labeling in testis was at or near background levels. CRF-RB$_1$ mRNA signal over duodenum appeared as a dense band of silver grains over the submucosal layer, and, additionally, over isolated non-epithelial cells at the base of the villi.

In the brain, CRF-RB$_1$ mRNA displayed a rather restricted distribution, which contrasts in extent and topography with that for CRF-RA$_1$ mRNA in rat. In the septal region, for example, CRF-RB$_1$ mRNA is expressed in circumscribed aspects of the lateral septal nucleus, while the CRF-RA$_1$ transcript is seen over the medial iseptal complex. Other major sites of CRF-RB$_1$ mRNA expression in the forebrain include circumscribed aspects of the olfactory bulb, preoptic region, hypothalamus, and amygdala.

In each of these areas, the pattern of CRF-RB$_1$ expression is seen to be distinct from that of the CRF-RA$_1$ in rat brain. It appears unlikely that major species differences in CRF-R distribution are at play, since the mouse CRF-RB1 probe employed here yielded similar patterns of hybridization in mouse and rat brain.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence (and the deduced amino acid sequence) of a cDNA encoding a human-derived CRF receptor of the present invention (i.e., hCRF-RA$_1$).

Sequence ID No. 2 is the deduced amino acid sequence of the human-derived CRF receptor set forth in Sequence ID No. 1.

Sequence ID No. 3 is the nucleic acid sequence (and the deduced amino acid sequence) of a splice variant cDNA insert encoding a 29 amino acid insert portion of the human-derived CRF receptor of the present invention. The splice variant cDNA insert is located between nucleotides 516–517 of Sequence ID No:1 (thereby producing CRF-RA$_2$).

Sequence ID No. 4 is the deduced amino acid sequence of the human-derived CRF receptor splice variant insert set forth in Sequence ID No. 3. The splice variant amino acid insert is located between amino acids 145–146 of SEQ ID NO:2.

Sequence ID No. 5 is the nucleic acid sequence (and the deduced amino acid sequence) of a cDNA encoding region of a rat-derived CRF receptor of the present invention (i.e., rCRF-RA).

Sequence ID No. 6 is the deduced amino acid sequence of the rat-derived CRF receptor set forth in Sequence ID No. 5.

Sequence ID No. 7 is the nucleic acid sequence (and the deduced amino acid sequence) of two exons (less the intervening intron sequence) of a partial genomic clone encoding a mouse-derived CRF receptor of the present invention (i.e. mCRF-RB$_1$).

Sequence ID No. 8 is the deduced amino acid sequence of the human-derived CRF receptor set forth in Sequence ID No. 7.

Sequence ID No. 9 is the nucleic acid sequence (and the deduced amino acid sequence) of a cDNA encoding a type-B mouse-derived CRF receptor of the present invention (i.e., mCRF-RB$_1$).

Sequence ID No. 10 is the deduced amino acid sequence of the mouse-derived CRF-RB receptor set forth in Sequence ID No. 9.

Sequence ID No. 11 is the "sense" probe described in Example 7.

Sequence ID No. 12 is the "antisense" probe described in Example 7.

Sequence ID No. 13 is the amino acid sequence of the mouse-derived CRF-RA$_1$ receptor.

Sequence ID No. 14 is the nucleotide sequence of a splice variant cDNA including an insert encoding a 29 amino acid portion of the human-derived CRF receptor of the present invention. The splice variant cDNA insert is located between nucleotides 516–517 of Sequence ID No:1 (thereby producing CRF-RA$_2$).

Sequence ID No. 15 is the amino sequence of a splice variant CRF (CRF-RA$_2$) including a 29 amino acid portion of the human-derived CRF receptor of the present invention. The splice variant amino acid insert is located between amino acids 145–146 of SEQ ID NO:2.

That which is claimed is:

1. A cell line expressing a recombinant CRF receptor encoded by a nucleic acid expression vector which:
   (a) encodes the amino acid sequence set forth in SEQ ID NO:2;
   (b) encodes the amino acid sequence encoded by the CRF-R encoding portion of clone hctCRFR, deposited with the ATCC under accession number 75474; or
   (c) hybridizes to the complement of the nucleic acid of (a) or (b) under low stringency conditions comprising a temperature of 42.5 degrees C., a formamide concentration of 20%, and a salt concentration of 5×SSC at pH 7.5, wherein said nucleic acid encodes CRF-R that binds CRF.

2. A cell line containing a nucleic acid vector encoding a recombinant CRF receptor, wherein said nucleic acid:
   (a) encodes the amino acid sequence set forth in SEQ ID NO:2;
   (b) encodes the amino acid sequence encoded by the CRF-R encoding portion of clone hctCRFR, deposited with the ATCC under accession number 75474; or
   (c) hybridizes to the complement of the nucleic acid of (a) or (b) under low stringency conditions comprising a temperature of 42.5 degrees C., a formamide concentration of 20%, and a salt concentration of 5×SSC at pH 7.5, wherein said nucleic acid encodes CRF-R that binds CRF.

3. A method for expressing a recombinant CRF receptor in a suitable host cell, said method comprising expressing a nucleic acid expression vector which:
   (a) encodes the amino acid sequence set forth in SEQ ID NO:2;
   (b) encodes the amino acid sequence encoded by the CRF-R encoding portion of clone hctCRFR, deposited with the ATCC under accession number 75474; or
   (c) is naturally occurring nucleic acid that hybridizes to the complement of the nucleic acid of (a) or (b) under low stringency conditions comprising a temperature of 42.5 degrees C., a formamide concentration of 20%, and a salt concentration of 5×SSC at pH 7.5, wherein said nucleic acid encodes CRF-R that binds CRF, or nucleic acid degenerate to said naturally occurring nucleic acid.

* * * * *